United States Patent [19]
Wieczorek

[11] Patent Number: 5,847,201
[45] Date of Patent: Dec. 8, 1998

[54] N-PROTECTED/N-SUBSTITUTED-BETA-AMINO HYDROXY SULFONATES

[75] Inventor: Joseph J. Wieczorek, Cary, Ill.

[73] Assignee: G.D. Searle & Co., Chicago, Ill.

[21] Appl. No.: 747,825

[22] Filed: Nov. 13, 1996

Related U.S. Application Data

[60] Provisional application No. 60/006,860 Nov. 16, 1995.
[51] Int. Cl.$^6$ .................................................. C07C 309/14
[52] U.S. Cl. ............................................................. 562/43
[58] Field of Search ................................................ 562/43

[56] References Cited

U.S. PATENT DOCUMENTS 4,990,669  2/1997  Reetz et al. .

FOREIGN PATENT DOCUMENTS

| | | |
|---|---|---|
| 393 457 B1 | 10/1990 | European Pat. Off. . |
| 888288 | 1/1962 | United Kingdom . |
| 2 020 648 | 11/1979 | United Kingdom . |
| 93/23368 | 11/1993 | WIPO . |
| 93/23388 | 11/1993 | WIPO . |
| 94/04491 | 3/1994 | WIPO . |
| 94/04492 | 3/1994 | WIPO . |
| 94/04493 | 3/1994 | WIPO . |
| 95/14653 | 6/1995 | WIPO . |

OTHER PUBLICATIONS

Mar., Advance Organic Chemistry, p. 895, 1992.
Parikh, et al., "Sulfur Trioxide in the Oxidation of Alcohols by Dimethyl Sulfoxide," J. Am. Chem. Soc., 89:21, 5505–5507, Oct. 11, 1967.
Mancuso, et al., "Oxidation of Long–Chain and Related Alcohols to Carbonyls by Dimethyl Sulfoxide 'Activated' by Oxalyl Chloride," J. Org. Chem., vol. 43, No. 12, 2480–2482, 1978.
Rittle, et al., "A Synthesis of Statine Utilizing an Oxidation Route to Chiral α–Amino Aldehydes," J. Org. Chem., vol. 47, 3016–3018, 1982.
Dellaria, et al., "The Enatino–And Diastereoselective Synthesis of the First Phospho–Staine Derivative," Tetrahedron Letters, vol. 27, No 21., 2337–2340, 1986.

Garner, et al., "The Synthesis and Configurational Stability of Differentially Protected β–Hydroxy–α–amino Aldehydes," J. Org. Chem., vol. 52, 2361–2364, 1987.
Reetz, et al., "Tandem Aldolization/Lactonization/Dyrotropic Rearrangement of α–AminoAldehydes," Tetrahedron Letters, vol. 30, No. 40., 5421–5424, 1989.
Jurczak, et al., "Optically Active N–Protected α–Amino Aldehydes in Organic Synthesis," Chem. Rev., Vol. 89,149–164, 1989
Reetz, et al., "Steroselective Reactions of Chiral α–Amino Aldehydes," Phil. Trans. R. Soc. Lond., A 326, 573–578 (1988).
Hamada, et al., "New Methods and Reagents in Organic Synthesis, A Practical Method for the Preparation of Optically Active N–Protected α–Amino Aldehydes and Peptice Aldehydes" Chem. Pharm. Bull. 30(5) 1921–1924, 1982.
Lubell, et al., "Configurational Stability of N–Protected α–Amino Aldehydes," J. Am. Chem. Soc., 109, 236–239, 1987.
Reetz, et al., "Steroselective Synthesis of β–Amino Alcohols from Optically Active α–Amino Acids," Angew. Chem. Int. Ed. Engl. 26, No. 11, 1987.
Khusid, "Regeneration of Aldehydes From Their Bisulfite Derivatives In Water and Organic Solvents On Ion–Exchange Resins," J. Org. Chem. of the USSR, vol. 21, No. 1, 37–39.
Érman, et al., "Structure and Properties of the Bisulfite Adducts of Citral," J. Org. Chem. of the USSR, vol. 15, No. 8, 1246–1431.
Ingles, "Preparation of Bisulphite Addition Compounds of 5–amino–5–deoxy–D–xylose," Australian J. Of Org. Chem., vol. 19, No. 4, 667–673 (copy unavailable at this time).

*Primary Examiner*—Robert Gerstl
*Attorney, Agent, or Firm*—Banner & Witcoff, LTD.

[57] ABSTRACT

N-protected/N-substituted alpha-amino aldehydes, which are useful as pharmaceuticals and pharmaceutical intermediates, can be stored and shipped in a more stable form as N-protected/N-substituted-beta-amino hydroxy sulfonates which can be readily converted back into the aldehyde under mild conditions. The present invention relates to N-protected/N-substituted-beta-amino hydroxy sulfonates and their preparation and use.

16 Claims, No Drawings

N-PROTECTED/N-SUBSTITUTED-BETA-AMINO HYDROXY SULFONATES

This application claims priority benefits from U.S. provisional application Ser. No. 60/006,860 filed Nov. 16, 1995.

BACKGROUND OF THE INVENTION

Synthesis of many pharmaceuticals, such as aspartyl protease inhibitors, involve the preparation of beta-amino alcohol intermediates from N-protected/N-substituted alpha-amino aldehydes in one or more steps. In particular, pharmaceuticals containing at least one chiral center can be prepared from chiral N-protected/N-substituted alpha-amino aldehydes. Examples of the preparation of chiral N-protected/N-substituted alpha-amino aldehydes and their use as pharmaceutical intermediates in the preparation of aspartyl protease inhibitors, such as renin and HIV protease inhibitors, dietetic sweeteners, bestatin derivatives can be found in Chem. Pharm. Bull. 30:1921–1924, 1982; J. Org. Chem. 43:2480–2482, 1978; J. Org. Chem. 47:3016–3018, 1982; Tet. Let. 27:2337–2340, 1986; PCT/US94/12201; WO 93/23388; WO 94/04491; WO 94/04492; WO 94/04493; U.S. Pat. No. 4,990,669; Tet. Let. 30:5421–5424, 1989; Philos. Trans. R. Soc. London, A, 326:573–578, 1988; Chem. Rev. 89:149–164, 1989; and J. Org. Chem. 52:2361–2364, 1987. In addition, N-substituted alpha-amino aldehydes are known to have cysteine proteinase inhibition activity, such as papin, calpain and cathepsin inhibition (see for example EP 393457).

A drawback to the use of N-protected/N-substituted alpha-amino aldehydes is their instability to storage, particularly long term storage, (see U.S. Pat. No. 4,990,669; Chem. Rev. 89:149–164, 1989; J. Org. Chem. 47:3016–3018, 1982; and J. Am. Chem. Soc. 109:236–239, 1987). This is particularly true for use of N-protected/N-substituted alpha-amino aldehydes in manufacturing processes, where it is sometimes advantageous to store and ship large quantities of intermediates, such as the N-protected/N-substituted alpha-amino aldehydes, to other locations for processing. Generally, N-protected/N-substituted alpha-amino aldehydes are used promptly following preparation and are not shipped or stored for long periods. Some efforts have been made to form configurationally stable derivatives of N-protected/N-substituted alpha-amino aldehydes (see J. Org. Chem. 52:2361–2364, 1987; and J. Am. Chem. Soc. 109:236–239, 1987), but such derivatives are not always applicable and the aldehyde group may still be unstable to long term storage, for example, due to air oxidation to the corresponding carboxylic acid, trimerization to the corresponding 1,3,5-trioxanes, and the like.

SUMMARY OF THE INVENTION

The present invention relates to a stabilized form of N-protected/N-substituted alpha-amino aldehydes, in particular, N-protected/N-substituted-beta-amino hydroxy sulfonates, and their preparation and use. An N-protected/N-substituted alpha-amino aldehyde can be stored for extended periods in the form of a N-protected/N-substituted-beta-amino hydroxy sulfonate which can be readily prepared and converted back into the N-protected/N-substituted alpha-amino aldehyde under mild conditions.

DETAILED DESCRIPTION OF THE INVENTION

This invention relates to the preparation and use of N-protected/N-substituted-beta-amino hydroxy sulfonates, a stabilized form of N-protected/N-substituted alpha-amino aldehydes, having the formula

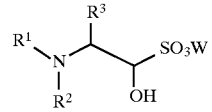

wherein W represents a cation which is capable of forming a sulfate salt; preferably, W represents a metal cation or a quaternary amine cation; more preferably, W represents a mono- or divalent metal cation; even more preferably, W represents a cation of lithium, sodium, potassium, calcium, manganese, magnesium, barium, chromium, iron, nickel, cobalt, copper, zinc, cadmium, tin or silver; even more preferably, W represents a cation of lithium, sodium, potassium, calcium, magnesium, barium, iron, nickel, copper or zinc; most preferably, W represents a cation of lithium, sodium or potassium;

$R^1$ represents alkyl, alkenyl, alkyl substituted with one or more aryl radicals, cycloalkenylalkyl, alkanoyl, haloalkanoyl, aroyl, alkoxycarbonyl, aralkoxycarbonyl, heteroaralkoxycarbonyl or 9-phenylfluoren-9-yl radicals; preferably, $R^1$ represents alkyl of 1–8 carbon atoms, alkenyl of 2–8 carbon atoms, alkyl of 1–3 carbon atoms substituted with 1–3 aryl radicals, alkyl of 1–3 carbon atoms substituted with a cycloalkenyl radical of 3–8 ring members, alkanoyl of 1–4 alkyl carbon atoms, haloalkanoyl of 1–4 alkyl carbon atoms and 1–3 halo radicals, aroyl, alkoxycarbonyl of 1–8 alkyl carbon atoms, arylmethoxycarbonyl, heteroarylmethoxycarbonyl or 9-phenylfluoren-9-yl radicals; more preferably, $R^1$ represents alkyl of 1–5 carbon atoms, alkenyl of 2–5 carbon atoms, alkyl of 1–2 carbon atoms substituted with 1–3 aryl radicals, alkyl of 1–2 carbon atoms substituted with a cycloalkenyl radical of 5–6 ring members, alkanoyl of 1–4 alkyl carbon atoms, haloalkanoyl of 1–2 alkyl carbon atoms and 1–3 halo radicals, aroyl, alkoxycarbonyl of 1–5 alkyl carbon atoms, arylmethoxycarbonyl, heteroarylmethoxycarbonyl or 9-phenylfluoren-9-yl radicals; even more preferably, $R^1$ represents methyl, ethyl, ethenyl, propenyl, benzyl, diphenylmethyl, naphthylmethyl, trityl, cyclohexenylmethyl, acetyl, butyryl, chloroacetyl, fluoroacetyl, difluoroacetyl, trifluoroacetyl, benzoyl, 2-methylbenzoyl, 2,6-dimethylbenzoyl, 2,4,6-trimethylbenzoyl, 2,4,6-triisopropylbenzoyl, methoxycarbonyl, ethoxycarbonyl, tert-butoxycarbonyl, phenylmethoxycarbonyl, (2-methylphenyl)methoxycarbonyl, isobutoxycarbonyl, (4-methylphenyl)methoxycarbonyl, (4-methoxyphenyl)methoxycarbonyl, pyridylmethoxycarbonyl, or 9-phenylfluoren-9-yl radicals; most preferably, $R^1$ represents methyl, ethyl, benzyl, diphenylmethyl, naphthylmethyl, trityl, trifluoroacetyl, tert-butoxycarbonyl, phenylmethoxycarbonyl or (4-methoxyphenyl)methoxycarbonyl radicals;

$R^2$ represents hydrogen, alkyl, alkenyl, aralkyl, cycloalkyl, cycloalkenylalkyl or aryl radicals; preferably, $R^2$ represents hydrogen, alkyl of 1–8 carbon atoms, alkenyl of 2–8 carbon atoms, alkyl of 1–3 carbon atoms substituted with an aryl radical, cycloalkyl of 3–8 ring members, alkyl of 1–3 carbon atoms substituted with a cycloalkenyl radical of 3–8 ring members, or aryl radicals; more preferably, $R^2$ represents hydrogen, alkyl of 1–5 carbon atoms, alkenyl of 2–5 carbon atoms, alkyl of 1–2 carbon atoms substituted with an aryl radical, cycloalkyl of 3–6 ring members, alkyl of 1–2 carbon atoms substituted with a cycloalkenyl radical of 5–6 ring members, or aryl radicals; even more preferably, $R^2$ represents methyl, ethyl, ethenyl, propenyl, benzyl, cyclohexenylmethyl or naphthylmethyl radicals; most preferably, $R^2$ represents methyl, ethyl or benzyl radicals; or —$NR^1R^2$ represents heterocyclo or heteroaryl radicals; preferably, —$NR^1R^2$ represents 5–6 ring membered heterocyclo, 5–6 ring membered heteroaryl, benzo fused 5–6 ring membered heterocyclo or benzo fused 5–6 ring membered heteroaryl radicals; more preferably, —$NR^1R^2$ represents 5–6 ring membered heterocyclo or benzo fused 5–6 ring membered heterocyclo radicals; even more preferably, —$NR^1R^2$ represents pyrrolidinyl, piperidinyl, pyrrolyl, 2-isoindolinyl, phthalimidyl, succinimidyl or maleimidyl radicals; most preferably, —$NR^1R^2$ represents 2-isoindolinyl, phthalimidyl, succinimidyl or maleimidyl radicals;

$R^3$ represents alkyl, alkenyl, alkynyl, haloalkyl, cyanoalkyl, hydroxyalkyl, alkoxyalkyl, aryloxyalkyl, alkylthioalkyl, arylthioalkyl, aryl, aralkyl, heteroaryl, heteroaralkyl, cycloalkyl or cycloalkylalkyl radicals; preferably, $R^3$ represents alkyl radical of 1 to 5 carbon atoms, alkenyl of 2–8 carbon atoms, alkynyl of 2–8 carbon atoms, haloalkyl radical of 1 to 5 carbon atoms, cyanoalkyl radical of 1 to 5 alkyl carbon atoms, hydroxyalkyl radical of 1 to 5 alkyl carbon atoms, alkoxyalkyl radical of 1 to 5 alkyl carbon atoms and 1–3 alkoxy carbon atoms, aryloxyalkyl radical of 1 to 5 alkyl carbon atoms, alkylthioalkyl radical of 1 to 5 alkyl carbon atoms and 1–3 alkylthio carbon atoms, arylthioalkyl radical of 1 to 5 alkyl carbon atoms, aryl radical, aralkyl radical of 1 to 5 alkyl carbon atoms, heteroaralkyl radical of 1 to 5 alkyl carbon atoms and 5–6 ring members and benzo fused 5–6 ring members, cycloalkyl radical of 3–8 ring members, or cycloalkylalkyl radical of 1 to 5 alkyl carbon atoms and 3–8 ring members; more preferably, $R^3$ represents alkyl radical of 1 to 5 carbon atoms, hydroxyalkyl radical of 1 to 3 alkyl carbon atoms, methoxyalkyl radical of 1 to 3 alkyl carbon atoms, phenoxyalkyl radical of 1 to 3 alkyl carbon atoms, methylthioalkyl radical of 1 to 3 alkyl carbon atoms, arylthioalkyl radical of 1 to 3 alkyl carbon atoms, aryl radical, aralkyl radical of 1 to 3 alkyl carbon atoms, heteroaralkyl radical of 1 to 3 alkyl carbon atoms and 5–6 ring members and benzo fused 5–6 ring members, cycloalkyl radical of 5–6 ring members, or cycloalkylalkyl radical of 1 to 3 alkyl carbon atoms and 3–6 ring members; even more preferably, $R^3$ represents methyl, ethyl, propyl, isopropyl, butyl, isobutyl, sec-butyl, tert-butyl, hydroxymethyl, hydroxyethyl, methoxyethyl, phenoxymethyl, methylthioethyl, phenylthiomethyl, phenylthioethyl, naphthylthiomethyl, naphthylthioethyl, phenyl, naphthyl, benzyl, 4-fluorobenzyl, 4-methylbenzyl, 4-methoxybenzyl, naphthylmethyl, imidazolylmethyl, indolylmethyl, cyclohexyl or cyclohexylmethyl radicals; most preferably, $R^3$ represents methyl, isopropyl, butyl, isobutyl, sec-butyl, tert-butyl, methylthioethyl, phenylthiomethyl, naphthylthiomethyl, benzyl, 4-fluorobenzyl, 4-methylbenzyl, 4-methoxybenzyl, naphthylmethyl, imidazolylmethyl or cyclohexylmethyl radicals; or $R^2$ and $R^3$ together with nitrogen atom and the carbon atom to which they are bonded form a heterocyclo radical; preferably, $R^2$ and $R^3$ together with nitrogen atom and the carbon atom to which they are bonded form a 5–6 ring membered heterocyclo radical optionally substituted with hydroxy radical; more preferably, $R^2$ and $R^3$ together with nitrogen atom and the carbon atom to which they are bonded form pyrrolidinyl, 3-hydroxypyrrolidinyl, 4-hydroxypyrrolidinyl, piperidinyl, 3-hydroxypiperidinyl, 4-hydroxypiperidinyl or 5-hydroxypiperidinyl radicals; and most preferably $R^2$ and $R^3$ together with nitrogen atom and the carbon atom to which they are bonded form pyrrolidinyl or piperidinyl radicals.

As utilized herein, the term "alkyl", alone or in combination, means a straight-chain or branched-chain alkyl radical containing preferably from 1 to 8 carbon atoms, more preferably from 1 to 5 carbon atoms, most preferably 1 to 3 carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "alkenyl", alone or in combination, means a straight-chain or branched-chain hydrocarbon radical having one or more double bonds and containing preferably from 2 to 10 carbon atoms, more preferably from 2 to 8 carbon atoms, most preferably from 2 to 5 carbon atoms. Examples of suitable alkenyl radicals include ethenyl, propenyl, 2-methylpropenyl, 1,4-butadienyl and the like. The term "alkynyl", alone or in combination, means a straight-chain or branched chain hydrocarbon radical having one or more triple bonds and containing preferably from 2 to 10 carbon atoms, more preferably from 2 to 5 carbon atoms. Examples of alkynyl radicals include ethynyl, propynyl (propargyl), butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated monocyclic, bicyclic or tricyclic alkyl radical wherein each cyclic moiety contains preferably from 3 to 8 carbon atom ring members, more preferably from 3 to 7 carbon atom ring members, most preferably from 5 to 6 carbon atom ring members, and which may optionally be a benzo fused ring system which is optionally substituted as defined herein with respect to the definition of aryl. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as naphthyl and β-carbolinyl, and substituted ring systems, such as biphenyl, phenylpyridyl, naphthyl and diphenylpiperazinyl. The term "cycloalkylalkyl" means an alkyl radical as defined above which is substituted by a cycloalkyl radical as defined above. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like. The term "cycloalkenyl", alone or in combination, means an cycloalkyl radical as defined above which contains at least one double bond in the ring and is non-aromatic in character. The term "cycloalkenylalkyl" means cycloalkenyl radical as defined above which is attached to an alkyl radical as defined above. Examples of such cycloalkenyl and cycloalkenylalkyl radicals include cyclopropenyl, cyclobutenyl, cyclopentenyl, cyclohexenyl, dihydrophenyl, cyclopropenylmethyl, cyclobutenylmethyl, cyclopentenylmethyl, cyclohexenylmethyl, dihydrophenylmethyl, and the like. The term "benzo", alone or in combination, means the divalent radical $C_6H_4$= derived from benzene. The term "aryl", alone or in combination, means a phenyl or naphthyl radical which is optionally substituted with one or more substituents selected from alkyl, alkoxy, halogen, hydroxy, amino, nitro, cyano, haloalkyl, carboxy, alkoxycarbonyl, cycloalkyl, heterocyclo, alkanoylamino, amido, amidino, alkoxycarbonylamino, N-alkylamidino, alkylamino, dialkylamino, N-alkylamido, N,N-dialkylamido, aralkoxycarbonylamino, alkylthio, alkylsulfinyl, alkylsulfonyl and the like. Examples of aryl radicals are phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, piperazinylphenyl and the like. The terms "aralkyl", and "aralkoxy", alone or in combination, means an alkyl or alkoxy radical as defined above in which at least one hydrogen atom is replaced by an aryl radical as defined above, such as benzyl, benzyloxy, 2-phenylethyl, dibenzylmethyl, hydroxyphenylmethyl, methylphenylmethyl, diphenylmethyl, diphenylmethoxy, 4-methoxyphenylmethoxy and the like. The term "aralkoxycarbonyl", alone or in combination, means a radical of the formula aralkyl-O—C(O)— in which the term "aralkyl" has the significance given above. Examples of an aralkoxycarbonyl radical are benzyloxycarbonyl and 4-methoxyphenylmethoxycarbonyl. The term "aryloxy" means a radical of the formula aryl-O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The term "cycloalkylcarbonyl" means an acyl radical of the formula cycloalkyl-C(O)— in which the term "cycloalkyl", has the significance give above, such as cyclopropylcarbonyl, cyclohexylcarbonyl, adamantylcarbonyl, 1,2,3,4-tetrahydro-2-naphthoyl, 2-acetamido-1,2,3,4-tetrahydro-2-naphthoyl, 1-hydroxy-1,2,3,4-tetrahydro-6-naphthoyl and the like. The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl, and the like. The term "aroyl", means an acyl radical derived from an arylcarboxylic acid, "aryl" having the meaning given above. Examples of such aroyl radicals include substituted and unsubstituted benzoyl or napthoyl such as benzoyl, 4-chlorobenzoyl, 4-carboxybenzoyl, 4-(benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like. The term "heterocyclo," alone or in combination, means a saturated or partially unsaturated monocyclic, bicyclic or tricyclic heterocycle radical containing at least one, preferably 1 to 4, more preferably 1 to 2, nitrogen, oxygen or sulfur atom ring members and having preferably 3 to 8 ring members in each ring, more preferably 3 to 7 ring members in each ring and most preferably 5 to 6 ring members in each ring. "Heterocyclo" is intended to include sulfones, sulfoxides, N-oxides of tertiary nitrogen ring members, and carbocyclic fused and benzo fused ring systems. Such heterocyclo radicals may be optionally substituted on at least one, preferably 1 to 4, more preferably 1 to 2, carbon atoms by halogen, alkyl, alkoxy, hydroxy, oxo, aryl, aralkyl, heteroaryl, heteroaralkyl, amidino, N-alkylamidino, alkoxycarbonylamino, alkylsulfonylamino and the like, and/or on a secondary nitrogen atom (i.e., —NH—) by hydroxy, alkyl, aralkoxycarbonyl, alkanoyl, heteroaralkyl, phenyl or phenylalkyl, and/or on a tertiary nitrogen atom (i.e., =N—) by oxido. "Heterocycloalkyl" means an alkyl radical as defined above in which at least one hydrogen atom is replaced by a heterocyclo radical as defined above, such as pyrrolidinylmethyl, tetrahydrothienylmethyl and the like. The term "heteroaryl", alone or in combination, means an aromatic heterocyclo radical as defined above, which is optionally substituted as defined above with respect to the definitions of aryl and heterocyclo. Examples of such heterocyclo and heteroaryl groups are pyrrolidinyl, piperidinyl, piperazinyl, morpholinyl, thiamorpholinyl, pyrrolyl, phthalimide, succinimide, maleimide, imidazolyl (e.g., imidazol 4-yl, 1-benzyloxycarbonylimidazol-4-yl, etc.), pyrazolyl, pyridyl, (e.g., 2-(1-piperidinyl)pyridyl and 2-(4-benzyl piperazin-1-yl-1-pyridinyl, etc.), pyrazinyl, pyrimidinyl, furyl, tetrahydrofuryl, thienyl, tetrahydrothienyl and its sulfoxide and sulfone derivatives, triazolyl, oxazolyl, thiazolyl, indolyl (e.g., 2-indolyl, etc.), quinolinyl, (e.g., 2-quinolinyl, 3-quinolinyl, 1-oxido-2-quinolinyl, etc.), isoquinolinyl (e.g., 1-isoquinolinyl, 3-isoquinolinyl, etc.), tetrahydroquinolinyl (e.g., 1,2,3,4-tetrahydro-2-quinolyl, etc.), 1,2,3,4-tetrahydroisoquinolinyl (e.g., 1,2,3,4-tetrahydro-1-oxo-isoquinolinyl, etc.), quinoxalinyl, β-carbolinyl, 2-benzofurancarbonyl, 1-,2-,4- or 5-benzimidazolyl, methylenedioxyphen-4-yl, methylenedioxyphen-5-yl, ethylenedioxyphenyl, benzothiazolyl, benzopyranyl, benzofuryl, 2,3-dihydrobenzofuryl, benzoxazolyl, thiophenyl and the like. "Heteroaralkyl", means an alkyl radical as defined above in which at least one hydrogen atom is replaced by a heteroaryl radical as defined above, such as pyrrolylmethyl, thienylmethyl, pyridylmethyl, furylmethyl and the like. The term "cycloalkylalkoxycarbonyl" means an acyl group derived from a cycloalkylalkoxycarboxylic acid of the formula cycloalkylalkyl-O—COOH wherein cycloalkylalkyl has the meaning given above. The term "heterocycloalkoxycarbonyl", means an acyl radical derived from a heterocycloalkyl-O—COOH wherein heterocyclo has the meaning given above. The term "heteroaryloxycarbonyl" means an acyl radical derived from a carboxylic acid represented by heteroaryl-O—COOH wherein heteroaryl has the meaning given above. The terms "halogen" or "halo" mean fluorine, chlorine, bromine or iodine. The term "haloalkanoyl" means an alkanoyl radical having the meaning as defined above wherein one or more hydrogens are replaced with a halogen radical. Examples of such haloalkanoyl radicals include chloroacetyl, fluoroacetyl, difluoroacetyl, trifluoroacetyl, and the like. The term "leaving group" (L) generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate. The term "oxidizing agent" includes a single agent or a mixture of oxidizing reagents. Examples of mixtures of oxidizing reagents include sulfur trioxide-pyridine/dimethylsulfoxide, oxalyl chloride/dimethyl sulfoxide, acetyl chloride/dimethyl sulfoxide, acetyl anhydride/dimethyl sulfoxide, trifluoroacetyl chloride/dimethyl sulfoxide, toluenesulfonyl bromide/dimethyl sulfoxide, phosphorous pentachloride/dimethyl sulfoxide and isobutylchloroformate/dimethyl sulfoxide.

Cations which are capable of forming sulfate salts include metal cations, quaternary amine cations and the like, such as ammonium, tetramethylammonium, tetrabutylammonium, tri-butyloctylammonium, dodecyltrimethylammonium, methyltrihexylammonium, dodecyldimethyl(2-phenoxyethyl)ammonium, tetramethylphosphonium, tetrabutylphosphonium and the like, or cations of lithium, sodium, potassium, rubidium, beryllium, calcium, strontium, manganese, magnesium, barium, chromium, iron, lead, nickel, cobalt, aluminum, cesium, copper, zinc, cadmium, tin, silver, zirconium and the like. The term $HSO_3W$ is intended to include multi-valent cations, such as $(HSO_3)_2Ca$, $(HSO_3)_2Fe$, $(HSO_3)_3Fe$, and the like, and cations of mixed salts of bisulfite, such as $(HSO_3)(HO)Ca$, $(HSO_3)(NO_3)_2Fe$, and the like. Also, the group $—SO_3W$ is intended to include multi-valent cations, such as $(—SO_3)_2Ca$, $(—SO_3)_2Fe$, $(—SO_3)_3Fe$, and the like, and cations of mixed salts of bisulfite, such as $(—SO_3)(HO)Ca$, $(—SO_3)(NO_3)_2Fe$, and the like.

Procedures for preparing the compounds of Formula I are set forth below. It should be noted that the general procedure is shown as it relates to preparation of compounds having the specified stereochemistry, for example, wherein the absolute stereochemistry about the carbon bonded to the amino group is designated as (S). However, such procedures are generally applicable to those compounds of opposite configuration, e.g., where the stereochemistry about the carbon bonded to the amino group is (R). In addition, the compounds having the (S) stereochemistry can be utilized to produce those having the (R) stereochemistry. For example, a compound having the (R) stereochemistry can be inverted to the (S) stereochemistry using well-known methods, such as epimerization followed by isolation of the desired racemate.

A general scheme for the preparation of N-protected/N-substituted-beta-amino hydroxy sulfonates of the present invention and their conversion into N-protected/N-substituted alpha-amino aldehydes is shown in Scheme I below.

Scheme I

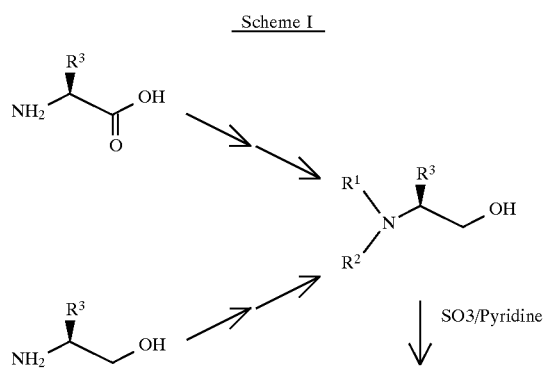

-continued
Scheme I

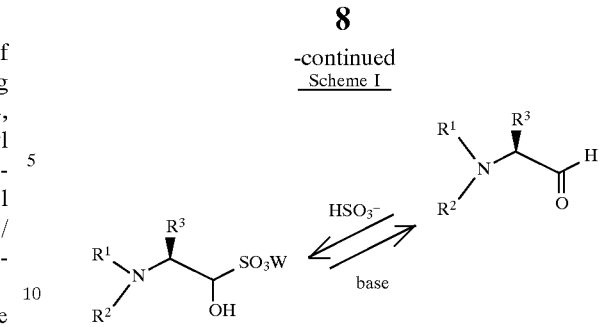

N-Protected/N-substituted alpha-amino aldehydes can be reacted with at least one equivalent of the bisulfite salt $HSO_3W$, preferably at an equivalence ratio within the range of about 1:1 to about 1:10, more preferably about 1:1 to about 1:5, and most preferably about 1:2 to about 1:5, in the appropriate solvent system, preferably, a mixture of water and an organic solvent such as ethyl acetate, tetrahydrofuran, isopropyl acetate, methyl isobutyl ketone, methyl ethyl ketone, acetone, dimethoxyethane, dimethoxymethane, dioxane, methyl tert-butylether and the like, to form the corresponding N-protected/N-substituted-beta-amino hydroxy sulfonates.

The aldehyde can be readily recovered by reacting the salt with aqueous base (pH>7.0), more preferably, at a pH in the range of about 7.5 to about 10 and most preferably, in the range of about 8 to about 9, followed by extraction with the appropriate organic solvent such as ethyl acetate and the like. The aqueous base is preferably aqueous sodium carbonate, potassium carbonate, sodium hydroxide, potassium hydroxide, ammonimum hydroxide, magnesium oxide, calcium oxide, and the like. The addition of an equilibrium exchange agent, such as formaldehyde, acetaldehyde, chloroacetaldehyde, benzaldehyde and the like, and preferably, a water soluble equilibrium exchange agent, such as formaldehyde, will assist in the reversion of the sulfonate into the corresponding aldehyde.

N-Protected/N-substituted alpha-amino aldehydes can be prepared economically and safely in small or large scales from either the corresponding amino acids or amino alcohols, which are commercially available or readily prepared from commercially available starting materials, using methods well known in the art.

N-Protected/N-substituted alpha-amino alcohol of the Formula II

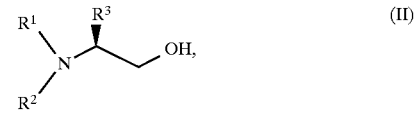

wherein $R^1$, $R^2$ and $R^3$ are described above, can be prepared from the corresponding amino acids or amino alcohols of Formulas III and IV

and

The amine group in each case can be alkylated in an appropriate solvent in the presence of base by the addition of suitable alkylating agents such as $R^2L$ and/or $R^1L$, wherein L is a leaving group selected from halo, tosylate, and the like, and $R^1$ and $R^2$ are as defined above. A preferred method of forming substituted amines involves the aqueous addition of about 3 moles of organic halide to the amino acid or about 2 moles to the amino alcohol. In an more preferred method, the alkylation occurs at 50° C. to 80° C. with potassium carbonate in water, ethanol/water or denatured ethanol/water. Additives such as sodium or potassium bromide, sodium or potassium iodide can catalyze or accelerate the rate of amine alkylation, especially when benzyl chloride was used as the nitrogen alkylating agent.

Alternate bases used in alkylation include sodium hydroxide, sodium bicarbonate, potassium hydroxide, lithium hydroxide, potassium carbonate, sodium carbonate, cesium hydroxide, magnesium hydroxide, calcium hydroxide or calcium oxide, or tertiary amine bases such as triethylamine, diisopropylethylamine, N-methylpiperidine, pyridine, dimethylaminopyridine and azabicyclononane. Reactions can be homogenous or heterogenous. Suitable solvents are water and protic solvents or solvents miscible with water, such as methanol, ethanol, isopropyl alcohol, tetrahydrofuran and the like, with or without added water. Dipolar aprotic solvents may also be used with or without added protic solvents including water. Examples of dipolar aprotic solvents include acetonitrile, dimethylformamide, dimethyl acetamide, acetamide, tetramethyl urea and its cyclic analog, dimethylsulfoxide, N-methylpyrrolidone, sulfolane, nitromethane and the like. Reaction temperature can range between about −20° to 100° C. with the preferred temperature of about 25°–85° C. The reaction may be carried out under an inert atmosphere such as nitrogen or argon, or normal or dry air, under atmospheric pressure or in a sealed reaction vessel under positive pressure. The most preferred alkylating agents are benzyl bromide or benzyl chloride or monosubstituted aralkyl halides or polysubstituted aralkyl halides. Sulfate or sulfonate esters are also suitable reagents to provide the corresponding benzyl analogs and they can be preformed from the corresponding benzyl alcohol or formed in situ by methods well known to those skilled in the art. Trityl, benzhydryl, substituted trityl and substituted benzhydryl groups, independently, are also effective amine protecting groups as are allyl and substituted allyl groups. Their halide derivatives can also be prepared from the corresponding alcohols by methods well known to those skilled in the art such as treatment with thionyl chloride or bromide or with phosphorus tri- or pentachloride, bromide or iodide or the corresponding phosphoryl trihalide. 1,2-Bis-substituted alkylene halides or sulfonate esters and benzo fused derivatives thereof can be used to form a nitrogen containing heteroaryl or heterocyclo containing compounds. Phase transfer catalysis wherein the amine and the alkylating agent are reacted with base in a solvent mixture in the presence of a phase transfer reagent, catalyst or promoter. The mixture can consist of, for example, toluene, benzene, ethylene dichloride, cyclohexane, methylene chloride or the like with water or a aqueous solution of an organic water miscible solvent such as THF. Examples of phase transfer catalysts or reagents include tetrabutylammonium chloride or iodide or bromide, tetrabutylammonium hydroxide, tri-butyloctylammonium chloride, dodecyltrihexylammonium hydroxide, methyltrihexylammonium chloride and the like.

Alternatively, the amino group can be reductively alkylated with an aldehyde or ketone to introduce the $R^1$ and/or $R^2$ groups. For example, when $R^1$ and $R^2$ represent benzyl groups, treatment of the amine with benzaldehyde under reductive amination conditions affords the desired N,N-dibenzylamine intermediate. Similarly, when $R^2$ is an cyclohexyl group, treatment the amine with cyclohexanone under reductive amination conditions affords the desired N-cyclohexylamine intermediate. Other aldehydes and ketones can be used to introduce various $R^1$ and $R^2$ groups. Reductive amination can be performed using a variety of reaction conditions well-known to those skilled in the art. For example, the reductive amination of the amine with an aldehyde can be carried out with a reducing agent such as sodium cyanoborohydride or sodium borohydride in a suitable solvent, such as methanol, ethanol, tetrahydrofuran and the like. Alternatively, the reductive amination can be carried out using hydrogen in the presence of a catalyst such as palladium or platinum, palladium on carbon or platinum on carbon, or various other metal catalysts known to those skilled in the art, in a suitable solvent such as methanol, ethanol, tetrahydrofuran, ethyl acetate, toluene and the like.

Alternatively, N-protected/N-substituted alpha-amino alcohol and acids can be prepared by reduction of a Schiff Base, carbinolamine or enamine or reduction of an acylated amine derivative. Reducing agents include metals [platinum, palladium, palladium hydroxide, palladium on carbon, platinum oxide, rhodium and the like] with hydrogen gas or hydrogen transfer molecules such as cyclohexene or cyclohexadiene or hydride agents such as lithium aluminumhydride, sodium borohydride, lithium borohydride, sodium cyanoborohydride, diisobutylaluminum hydride or lithium tri-tert-butoxyaluminum hydride.

The N-protected/N-substituted alpha-amino alcohol can then be prepared by reduction of the corresponding N-protected/N-substituted alpha-amino acid of formula

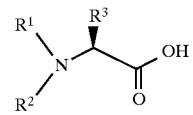

or an ester or amide thereof. This process is particularly suitable when hydroxy groups are present in the molecule. The hydroxy groups can be selectively protected, using well known hydroxy protecting groups, prior to formation of the N-protected/N-substituted alpha-amino alcohol and thus allowing selective oxidation of the alcohol group to an aldehyde moiety. The hydroxy protecting groups are then removed after formation of the aldehyde. The reduction can be accomplished using a variety of reducing reagents and conditions. Reducing agents include metals [platinum, palladium, palladium hydroxide, palladium on carbon, platinum oxide, rhodium and the like] with hydrogen gas or hydrogen transfer molecules such as cyclohexene or cyclohexadiene or hydride agents such as lithium aluminumhydride, diborane•tetrahydrofuran, sodium borohydride, lithium borohydride, sodium cyanoborohydride, diisobutylaluminum hydride or lithium tri-tert-butoxyaluminum hydride. Preferred reducing agents include lithium aluminum hydride, lithium borohydride, sodium borohydride, borane, lithium tri-ter-butoxyaluminum hydride, and diborane•tetrahydrofuran. Most preferably, the reducing agent is lithium aluminum hydride, diborane•tetrahydrofuran or diisobutylaluminum hydride (DiBAL-H) in toluene.

The above preparation of N-protected/N-substituted alpha-amino alcohol is applicable to mixtures of optical isomers as well as resolved compounds. If a particular optical isomer is desired, it can be selected by the choice of starting material, e.g., L-phenylalanine, D-phenylalanine, L-phenylalaninol, D-phenylalaninol, D-hexahydrophenylalaninol and the like, or resolution can occur at intermediate or final steps. Chiral auxiliaries such as one or two equivalents of camphor sulfonic acid, citric acid, camphoric acid, 2-methoxyphenylacetic acid and the like can be used to form salts, esters or amides of the starting materials of this invention. These compounds or derivatives can be crystallized or separated chromatographically using either a chiral or achiral column as is well known to those skilled in the art.

Purification of the N-protected/N-substituted alpha-amino alcohol by chromatography is possible. In the preferred purification method the alpha amino alcohol can be purified by an acid quench of the reaction, such as with hydrochloric acid, and the resulting salt can be filtered off as a solid and the amino alcohol can be liberated such as by acid/base extraction.

The N-protected/N-substituted alpha-amino alcohol is oxidized to form a chiral amino aldehyde of the formula

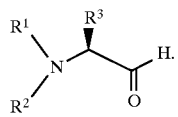

Acceptable oxidizing reagents include, for example, sulfur trioxide-pyridine complex and DMSO, oxalyl chloride and DMSO, acetyl chloride or anhydride and DMSO, trifluoroacetyl chloride or anhydride and DMSO, methanesulfonyl chloride and DMSO or tetrahydrothiaphene-S-oxide, toluenesulfonyl bromide and DMSO, trifluoromethanesulfonyl anhydride (triflic anhydride) and DMSO, phosphorus pentachloride and DMSO, dimethylphosphoryl chloride and DMSO and isobutylchloroformate and DMSO. The oxidation conditions reported in Angew Chem., 99:1186, 1987 (Angew Chem. Int. Ed. Engl., 26:1141, 1987), and J. Org. Chem. 43:2480–2482, 1978 employed oxalyl chloride and DMSO; and in J. Am. Chem. Soc., 89:5505, 1967, Chem. Pharm. Bull. 30:1921–1924, 1982, and J. Org. Chem. 47:3016–3018, 1982, employed SO$_3$/Pyridine complex in methylene chloride or DMSO and triethylamine. The preferred oxidation method is sulfur trioxide pyridine complex in triethylamine and DMSO at room temperature. The oxidation reaction may be carried out under an inert atmosphere such as nitrogen or argon, or normal or dry air, under atmospheric pressure or in a sealed reaction vessel under positive pressure. Preferred is a nitrogen atmosphere. Alternative amine bases include, for example, tri-butyl amine, tri-isopropyl amine, N-methylpiperidine, N-methyl morpholine, azabicyclononane, diisopropylethylamine, 2,2,6,6-tetramethylpiperidine, N,N-dimethylaminopyridine, or mixtures of these bases. Triethylamine is a preferred base. Alternatives to pure DMSO as solvent include mixtures of DMSO with non-protic or halogenated solvents such as tetrahydrofuran, ethyl acetate, toluene, xylene, dichloromethane, ethylene dichloride and the like. Dipolar aprotic co-solvents include acetonitrile, dimethylformamide, dimethylacetamide, acetamide, tetramethyl urea and its cyclic analog, N-methylpyrrolidone, sulfolane and the like.

Two additional methods of obtaining the nitrogen protected aldehyde include oxidation of the corresponding alcohol with bleach in the presence of a catalytic amount of 2,2,6,6-tetramethyl-1-pyridyloxy free radical. In a second method, oxidation of the alcohol to the aldehyde is accomplished by a catalytic amount of tetrapropylammonium perruthenate in the presence of N-methylmorpholine-N-oxide.

Alternatively, the N-protected/N-substituted alpha-amino aldehyde can be prepared directly from the corresponding N-protected/N-substituted alpha-amino acid. ester or amide by hydride reduction sodium amalgam with HCl in ethanol or lithium or sodium or potassium or calcium in ammonia. The reaction temperature may be from about −20° C. to about 45° C., and preferably from abut 5° C. to about 25° C. Hydride transfer is an additional method of aldehyde synthesis under conditions where aldehyde condensations are avoided, cf, Oppenauer Oxidation. Alternatively, the acid halide derivative, such as acid chloride, can be reduced with hydrogen and a catalyst such as Pd on barium carbonate or barium sulphate, with or without an additional catalyst moderating agent such as sulfur or a thiol (Rosenmund Reduction). Such methods are preferred when hydroxy groups are present in the molecule. This approach will generally avoid the necessity of protecting and deprotecting the alcohol groups.

Scheme II is an illustrative example of alternative preparation methods of 2S-[bis(phenylmethyl)amino]-3-phenylpropanal.

Scheme II

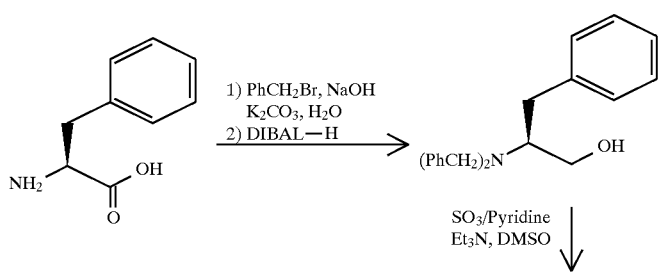

-continued
Scheme II

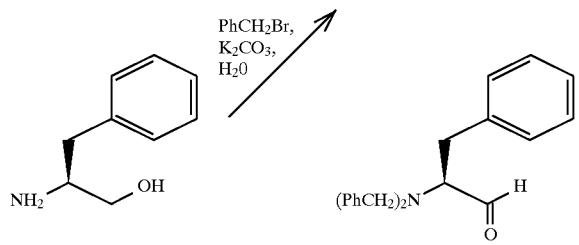

The synthesis starts from L-phenylalanine. The aldehyde is prepared in three steps from L-phenylalanine or L-phenylalaninol. L-Phenylalanine is converted to the N,N-dibenzylamino acid benzyl ester using benzyl bromide under aqueous conditions. The reduction of benzyl ester is carried out using diisobutylaluminum hydride (DIBAL-H) in toluene. Instead of purification by chromatography, the product is purified by an acid (hydrochloric acid) quench of the reaction, the hydrochloride salt is filtered off as a white solid and then liberated by an acid/base extraction. After one recrystallization, chemically and optically pure alcohol is obtained. Alternately, and preferably, the alcohol can be obtained in one step in 88% yield by the benzylation of L-phenylalaninol using benzylbromide under aqueous conditions. The oxidation of alcohol to aldehyde is also modified to allow for more convenient operation during scaleup. Instead of the standard Swern procedures using oxalyl chloride and DMSO in methylene chloride at low temperatures, sulfur trioxide-pyridine/DMSO was employed (J. Am. Chem. Soc., 89:5505, 1967) which can be conveniently performed at room temperature to give excellent yields of the desired aldehyde with high chemical and enantiomer purity which does not require purification.

Scheme III illustrates the preparation of 2S-[(tert-butoxycarbonyl)(phenylmethyl)amino]-3-phenylpropanal from L-phenylalaninol, where BOC is tert-butoxycarbonyl and Bn is benzyl.

Scheme IV

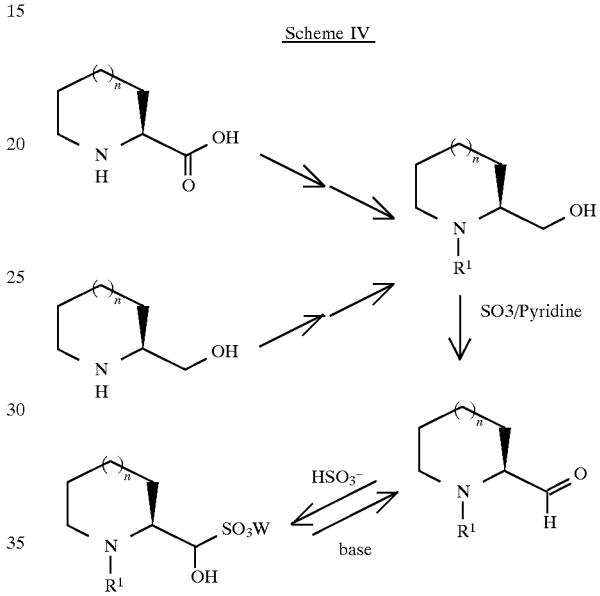

The chemical reactions described above are generally disclosed in terms of their broadest application to the preparation of the compounds of this invention.

Scheme III

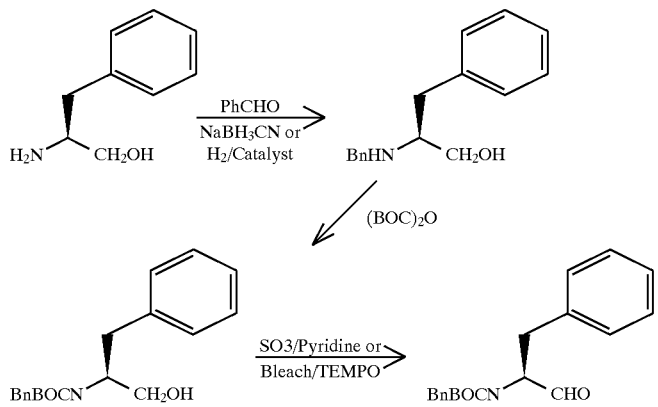

Scheme IV illustrates the preparation of N-protected/N-substituted-beta-amino hydroxy sulfonates of the present invention where $R^2$ and $R^3$ together with nitrogen atom and the carbon atom to which they are bonded form a heterocyclo radical (n=0–1).

Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

All reagents were used as received without purification. All proton and carbon NMR spectra were obtained on either a Varian VXR-300 or VXR-400 nuclear magnetic resonance spectrometer.

The following Examples illustrate the preparation of inhibitor compounds of the present invention and intermediates useful in preparing the inhibitor compounds of the present invention.

EXAMPLE 1

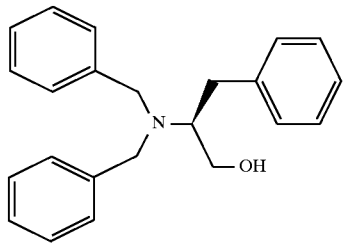

2S-[Bis(phenylmethyl)amino]-3-phenylpropanol
METHOD 1:
Step 1: Benzylation of L-Phenylalanine A solution of L-phenylalanine (50.0 g, 0.302 mol), sodium hydroxide (24.2 g, 0.605 mol) and potassium carbonate (83.6 g, 0.605 mol) in water (500 mL) was heated to 97° C. Benzyl bromide (108.5 mL, 0.605 mol) was then slowly added (addition time—25 min). The mixture was stirred at 97° C. for 30 minutes under a nitrogen atmosphere. The solution was cooled to room temperature and extracted with toluene (2×250 mL). The combined organic layers were washed with water and brine, dried over magnesium sulfate, filtered and concentrated to an oil. The identity of the product was confirmed as follows. Analytical TLC (10% ethyl acetate/hexane, silica gel) showed major component at Rf value=0.32 to be the desired tribenzylated compound, N,N-bis(phenylmethyl)-L-phenylalanine phenylmethyl ester. This compound can be purified by column chromatography (silica gel, 15% ethyl acetate/hexanes). Usually the product is pure enough to be used directly in the next step without further purification. $^1$H NMR spectrum was in agreement with published literature. $^1$H NMR (CDCL$_3$) δ, 3.00 and 3.14 (ABX-system, 2H, $J_{AB}$=14.1 Hz, $J_{AX}$=7.3 Hz and $J_{BX}$=5.9 Hz), 3.54 and 3.92 (AB-System , 4 H, $J_{AB}$=13.9 Hz), 3.71 (t, 1H, J=7.6 Hz), 5.11 and 5.23 (AB-System, 2H, $J_{AB}$=12.3 Hz), and 7.18 (m, 20 H). EIMS: m/z 434 (M-1).

Step 2: 2S-[Bis(phenylmethyl)amino]-3-phenylpropanol

N,N-Bis(phenylmethyl)-L-phenylalanine phenylmethyl ester (0.302 mol) from the previous reaction was dissolved in toluene (750 mL) and cooled to −55° C. A 1.5M solution of DIBAL in toluene (443.9 mL, 0.666 mol) was added at a rate to maintain the temperature between −55° to −50° C. (addition time—1 hr). The mixture was stirred for 20 minutes under a nitrogen atmosphere and then quenched at −55° C. by the slow addition of methanol (37 ml). The cold solution was then poured into cold (5°C.) 1.5N HCl solution (1.8 L). The precipitated solid (approx. 138 g) was filtered off and washed with toluene. The solid material was suspended in a mixture of toluene (400 mL) and water (100 ml). The mixture was cooled to 5° C. and treated with 2.5N NaOH (186 mL) and then stirred at room temperature until solid dissolved. The toluene layer was separated from the aqueous phase and washed with water and brine, dried over magnesium sulfate, filtered and concentrated to a volume of 75 mL (89 g). Ethyl acetate (25 mL) and hexane (25 mL) were added to the residue upon which the desired alcohol product began to crystallize. After 30 min, an additional 50 mL hexane were added to promote further crystallization. The solid was filtered off and washed with 50 mL hexane to give 34.9 g of first crop product. A second crop of product (5.6 g) was isolated by refiltering the mother liquor. The two crops were combined and recrystallized from ethyl acetate (20 mL) and hexane (30 mL) to give 40 g of 2S-[bis (phenylmethyl)amino]-3-phenylpropanol, 40% yield from L-phenylalanine. An additional 7 g (7%) of product can be obtained from recrystallization of the concentrated mother liquor. TLC of product Rf=0.23 (10% ethyl acetate/hexane, silica gel);$^1$H NMR (CDCl$_3$) δ 2.44 (m, 1H,), 3.09 (m, 2H), 3.33 (m, 1H), 3.48 and 3.92 (AB-System, 4H, $J_{AB}$=13.3 Hz), 3.52 (m, 1H) and 7.23 (m, 15H); [a]$_D$25+42.4 (c 1.45, CH$_2$Cl$_2$); DSC 77.67° C.; Anal. Calcd.for C$_{23}$H$_{25}$ON: C, 83.34; H, 7.60; N, 4.23. Found: C, 83.43; H, 7.59; N, 4.22. HPLC on chiral stationary phase: Cyclobond I SP column (250×4.6 mm I.D.), mobile phase: methanol/triethyl ammonium acetate buffer pH 4.2 (58:42, v/v), flow-rate of 0.5 ml/min, detection with detector at 230 nm and a temperature of 0° C. Retention time: 11.25 min., retention time of the desired product enantiomer: 12.5 min.

METHOD 2:

Preparation of 2S-[Bis(phenylmethyl)amino]-3-phenylpropanol

L-phenylalaninol (176.6 g, 1.168 mol) was added to a stirred solution of potassium carbonate (484.6 g, 3.506 mol) in 710 mL of water. The mixture was heated to 65° C. under a nitrogen atmosphere. A solution of benzyl bromide (400 g, 2.339 mol) in 3A ethanol (305 mL) was added at a rate that maintained the temperature between 60–68° C. The biphasic solution was stirred at 65° C. for 55 min and then allowed to cool to 10° C. with vigorous stirring. The oily product solidified into small granules. The product was diluted with 2.0 L of tap water and stirred for 5 minutes to dissolve the inorganic by products. The product was isolated by filtration under reduced pressure and washed with water until the pH is 7. The crude product obtained was air dried overnight to give a semi-dry solid (407 g) which was recrystallized from 1.1 L of ethyl acetate/heptane (1:10 by volume). The product was isolated by filtration (at −8° C.), washed with 1.6 L of cold (−10° C.) ethyl acetate/heptane (1:10 by volume) and air-dried to give 339 g (88% yield) of 2S-[Bis (phenylmethyl)amino]-3-phenylpropanol, mp 71.5°–73.0° C. More product can be obtained from the mother liquor if necessary. The other analytical characterization was identical to compound prepared as described in Method 1.

EXAMPLE 2

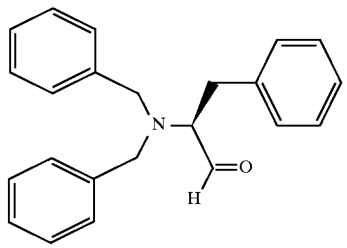

Preparation of 2S-[Bis(phenylmethyl)amino]-3-phenylpropanal

METHOD 1:

2S-[Bis(phenylmethyl)amino]-3-phenylpropanol (200 g, 0.604 mol) was dissolved in triethylamine (300 mL, 2.15 mol). The mixture was cooled to 12° C. and a solution of sulfur trioxide/pyridine complex (380 g, 2.39 mol) in DMSO (1.6 L) was added at a rate to maintain the temperature between 8–17° C. (addition time—1.0 h). The solution was stirred at ambient temperature under a nitrogen atmosphere for 1.5 hour at which time the reaction was complete by TLC analysis (33% ethyl acetate/hexane, silica gel). The reaction mixture was cooled with ice water and quenched with 1.6 L of cold water (10°–15° C.) over 45 minutes. The resultant solution was extracted with ethyl acetate (2.0 L), washed with 5% citric acid (2.0 L), and brine (2.2 L), dried over $MgSO_4$ (280 g) and filtered. The solvent was removed on a rotary evaporator at 35°–40° C. and then dried under vacuum to give 198.8 g of 2S-[Bis(phenylmethyl)amino]-3-phenylpropanal as a pale yellow oil (99.9%). The crude product obtained was pure enough to be used directly in the next step without purification. The analytical data of the compound were consistent with the published literature.[a] $_D25=-92.9°$ (c 1.87, $CH_2Cl_2$); $^1H$ NMR (400 MHz, $CDCl_3$) δ, 2.94 and 3.15 (ABX-System, 2H, $J_{AB}=13.9$ Hz, $J_{AX}=7.3$ Hz and $J_{BX}=6.2$ Hz), 3.56 (t, 1H, 7.1 Hz), 3.69 and 3.82 (AB-System, 4H, $J_{AB}=13.7$ Hz), 7.25 (m, 15 H) and 9.72 (s, 1H); HRMS calcd for (M+1) $C_{23}H_{24}NO$ 330.450, found: 330.1836. Anal. Calcd. for $C_{23}H_{23}ON$: C, 83.86; H, 7.04; N, 4.25. Found: C, 83.64; H, 7.42; N, 4.19. HPLC on chiral stationary phase:(S,S) Pirkle-Whelk-O 1 column (250×4.6 mm I.D.), mobile phase: hexane/isopropanol (99.5:0.5, v/v), flow-rate: 1.5 ml/min, detection with UV detector at 210 nm. Retention time of the desired S-isomer: 8.75 min., retention time of the R-enantiomer 10.62 min.

METHOD 2:

A solution of oxalyl chloride (8.4 ml, 0.096 mol) in dichloromethane (240 ml) was cooled to −74° C. A solution of DMSO (12.0 ml, 0.155 mol) in dichloromethane (50 ml) was then slowly added at a rate to maintain the temperature at −74° C. (addition time~1.25 hr). The mixture was stirred for 5 min. followed by addition of a solution of 2S-[bis (phenylmethyl)amino]-3-phenylpropanol (0.074 mol) in 100 ml of dichloromethane (addition time—20 min., temp. −75° C. to −68° C.). The solution was stirred at −78° C. for 35 minutes under a nitrogen atmosphere. Triethylamine (41.2 ml, 0.295 mol) was then added over 10 min. (temp. −78° to −68° C.) upon which the ammonium salt precipitated. The cold mixture was stirred for 30 min. and then water (225 ml) was added. The dichloromethane layer was separated from the aqueous phase and washed with water, brine, dried over magnesium sulfate, filtered and concentrated. The residue was diluted with ethyl acetate and hexane and then filtered to further remove the ammonium salt. The filtrate was concentrated to give 2S-[Bis(phenylmethyl)amino]-3-phenylpropanal. The aldehyde was generally used without purification.

METHOD 3:

To a mixture of 1.0 g (3.0 mmoles) of 2S-[bis (phenylmethyl)amino]-3-phenylpropanol 0.531 g (4.53 mmoles) of N-methylmorpholine, 2.27 g of molecular sieves (4A) and 9.1 mL of acetonitrile was added 53 mg (0.15 mmoles) of tetrapropylammonium perruthenate (TPAP). The mixture was stirred for 40 minutes at room temperature and concentrated under reduced pressure. The residue was suspended in 15 mL of ethyl acetate, filtered through a pad of silica gel. The filtrate was concentrated under reduced pressure to give a product containing approximately 50% of 2S-[Bis(phenylmethyl)amino]-3-phenylpropanal as a pale yellow oil.

METHOD 4:

To a solution of 1.0 g (3.02 mmoles) of 2S-[bis (phenylmethyl)amino]-3-phenylpropanol in 9.0 mL of toluene was added 4.69 mg(0.03 mmoles) of 2,2,6,6-tetramethyl-1-piperidinyloxy, free radical (TEMPO), 0.32 g (3.11 mmoles) of sodium bromide, 9.0 mL of ethyl acetate and 1.5 mL of water. The mixture was cooled to 0° C. and an aqueous solution of 2.87 mL of 5% household bleach containing 0.735 g(8.75 mmoles) of sodium bicarbonate and 8.53 mL of water was added slowly over 2.5 minutes. The mixture was stirred at 0° C. for 60 minutes. Two more additions (1.44 mL each) of bleach was added followed by stirring for 10 minutes. The two phase mixture was allowed to separate. The aqueous layer was extracted twice with 20 mL of ethyl acetate. The combined organic layer was washed with 4.0 mL of a solution containing 25 mg of potassium iodide and water(4.0 mL), 20 mL of 10% aqueous sodium thiosulfate solution and then brine solution. The organic solution was dried over magnesium sulfate, filtered and concentrated under reduced pressure to give 1.34 g of crude oil containing a small amount of 2S-[bis (phenylmethyl)amino]-3-phenylpropanal.

METHOD 5:

Following the same procedures as described in Method 1 except 3.0 equivalents of sulfur trioxide pyridine complex was used and 2S-[bis(phenylmethyl)amino]-3-phenylpropanal was isolated in comparable yields.

EXAMPLE 3

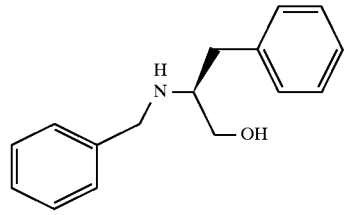

Preparation of N-Benzyl-L-phenylalaninol

METHOD 1:

L-Phenylalaninol (89.51 g, 0.592 moles) was dissolved in 375 mL of methanol under inert atmosphere, 35.52 g (0.592 moles) of glacial acetic acid and 50 mL of methanol was added followed by a solution of 62.83 g (0.592 moles) of benzaldehyde in 100 mL of methanol. The mixture was cooled to approximately 15° C. and a solution of 134.6 g (2.14 moles) of sodium cyanoborohydride in 700 mL of methanol was added in approximately 40 minutes, keeping the temperature between 15° C. and 25° C. The mixture was stirred at room temperature for 18 hours. The mixture was concentrated under reduced pressure and partitioned between 1 L of 2M ammonium hydroxide solution and 2 L of ether. The ether layer was washed with 1 L of 1M ammonium hydroxide solution, twice with 500 mL water, 500 mL of brine and dried over magnesium sulfate for 1 hour. The ether layer was filtered, concentrated under reduced pressure and the crude solid product was recrystallized from 110 mL of ethyl acetate and 1.3 L of hexane to give 115 g (81% yield) of N-benzyl-L-phenylalaninol as a white solid.

METHOD 2:

L-Phenylalaninol (5 g, 33 mmoles) and 3.59 g (33.83 mmoles) of benzaldehyde were dissolved in 55 mL of 3A ethanol under inert atmosphere in a Parr shaker and the mixture was warmed to 60° C. for 2.7 hours. The mixture was cooled to approximately 25° C. and 0.99 g of 5% platinum on carbon was added and the mixture was hydrogenated at 60 psi of hydrogen and 40° C. for 10 hours. The catalyst was filtered off, the product was concentrated under reduced pressure and the crude solid product was recrystallized from 150 mL of heptane to give 3.83 g(48% yield) of N-benzyl-L-phenylalaninol as a white solid.

EXAMPLE 4

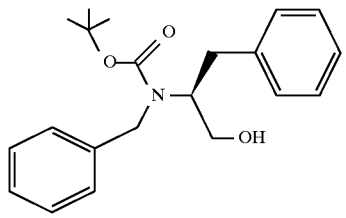

Preparation of N-(tert-Butoxycarbonyl)-N-benzyl-L-phenylalaninol

N-Benzyl-L-phenylalaninol (2.9 g, 12 mmoles) was dissolved in 3 mL of triethylamine and 27 mL of methanol and 5.25 g (24.1 mmoles) of di-tert-butyl dicarbonate was added. The mixture was warmed to 60° C. for 35 minutes and concentrated under reduced pressure. The residue was dissolved in 150 mL of ethyl acetate and washed twice with 10 mL of cold(0°–5° C.), dilute hydrochloric acid (pH 2.5 to 3), 15 mL of water, 10 mL of brine, dried over magnesium sulfate, filtered and concentrated under reduced pressure. The crude product oil was purified by silica gel chromatography (ethyl acetate:hexane, 12:3 as eluting solvent) to give 3.98 g (97% yield) of colorless oil.

EXAMPLE 5

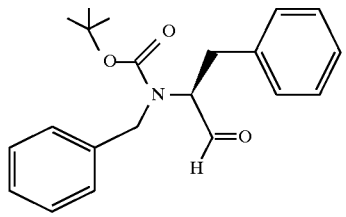

Preparation of N-(t-Butoxycarbonyl)-N-benzyl-L-phenylalaninal

METHOD 1:

To a solution of 0.32 g(0.94 mmoles) of N-(tert-butoxycarbonyl)-N-benzyl-L-phenylalaninol in 2.8 mL of toluene was added 2.4 mg (0.015 mmoles) of 2,2,6,6-tetramethyl-1-piperidinyloxy, free radical (TEMPO), 0.1 g (0.97 mmoles) of sodium bromide, 2.8 mL of ethyl acetate and 0.34 mL of water. The mixture was cooled to 0° C. and an aqueous solution of 4.2 mL of 5% household bleach containing 0.23 g (3.0 mL, 2.738 mmoles) of sodium bicarbonate was added slowly over 30 minutes. The mixture was stirred at 0° C. for 10 minutes. Three more additions (0.4 mL each) of bleach was added followed by stirring for 10 minutes after each addition to consume all the stating material. The two phase mixture was allowed to separate. The aqueous layer was extracted twice with 8 mL of toluene. The combined organic layer was washed with 1.25 mL of a solution containing 0.075 g of potassium iodide, sodium bisulfate (0.125 g) and water (1.1 mL), 1.25 mL of 10% aqueous sodium thiosulfate solution, 1.25 mL of pH 7 phosphate buffer and 1.5 mL of brine solution. The organic solution was dried over magnesium sulfate, filtered and concentrated under reduced pressure to give 0.32 g (100% yield) of N-(tert-butoxycarbonyl)-N-benzyl-L-phenylalaninal.

METHOD 2:

To a solution of 2.38 g (6.98 mmoles) of N-(tert-butoxycarbonyl)-N-benzyl-L-phenylalaninol in 3.8 mL (27.2 mmoles) of triethylamine at 10° C. was added a solution of 4.33 g (27.2 mmoles) of sulfur trioxide pyridine complex in 17 mL of dimethyl sulfoxide. The mixture was warmed to room temperature and stirred for one hour. Water (16 mL) was added and the mixture was extracted with 20 mL of ethyl acetate. The organic layer was washed with 20 mL of 5% citric acid, 20 mL of water, 20 mL of brine, dried over magnesium sulfate and filtered. The filtrate was concentrated under reduced pressure to give 2.37 g (100% yield) of N-(t-butoxycarbonyl)-N-benzyl-L-phenylalaninal.

EXAMPLE 6

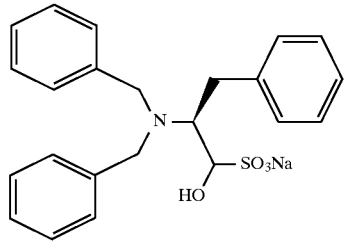

Preparation of 2S-[bis(phenylmethyl)amino]-1-hydroxy-3-phenylpropylsulfonic acid, sodium salt 2S-[Bis(phenylmethyl)amino]-3-phenylpropanal, which was stored at −80° C., was warmed from −80° C. until it became a syrup. Fifty grams (0.1518 mol) was dissolved in 200 mL of ethyl acetate at room temperature under a nitrogen atmosphere. Sodium bisulfite (NaHSO₃), 49.8 g (0.4544 mol), in 200 mL of water was added in a slow stream to the aldehyde solution. Vigorous stirring was maintained during the addition and the reaction. After about one hour, the ethyl acetate layer was separated and the solvent partially removed under vacuum on a rotary evaporator to provide a crystalline solid. The ethyl acetate solution was recombined with the sodium bisulfite and the ethyl acetate removed under vacuum. Ethyl acetate was added to the residue in 25 mL portions for a total of 75 mL and the white solid thus obtained separated by filtration. The solid was washed with ethyl acetate and dried under a nitrogen atmosphere and vacuum to yield 16 grams of 2S-[bis (phenylmethyl)amino]-1-hydroxy-3-phenylpropylsulfonic acid, sodium salt as a white solid. The assigned structure was confirmed by combustion analysis and infrared (IR) spectroscopy as a potassium bromide pellet. Combustion Analysis: Calculated for $C_{23}H_{24}NO_4SNa$ (433.50); C=63.73%, H=5.58%, N=3.23%, S=7.40%; Found: C=65.94%, 65.73%, H=6.27%, 6.28% N=3.35%, 3.26%, S=8.04%. There was no aldehyde carbonyl group in the IR spectrum.

EXAMPLE 7

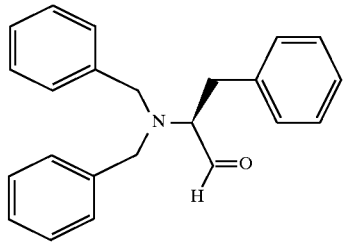

Preparation of 2S-[bis(phenylmethyl)amino]-3-phenylpropanal from 2S-[bis(phenylmethyl)amino]-1-hydroxy-3-phenylpropylsulfonic acid, sodium salt 2S-[Bis(phenylmethyl)amino]-1-hydroxy-3-phenylpropyl sulfonic acid, sodium salt (5 grams) was treated with stirring with an aqueous solution of 5 grams of potassium carbonate in 50 mL of water at room temperature. The aqueous solution was extracted once with a 50 mL portion of ethyl acetate. The organic solvent solutions were combined and removed under reduced pressure. The residue was dissolved in the tetrahydrofuran (THF), filtered through a cotton filter plug and the solvent removed under reduced pressure. The residue was again dissolved in THF and the solvent removed under reduced pressure to provide 4.1 grams of 2S-[bis(phenylmethyl)amino]-3-phenylpropanal as a colorless oil whose identity was confirmed by high performance liquid chromatography (HPLC) using Whatman Partisil 5 column 25 cm in length with a 4.6 mm i.d. at ambient (room) temperature. Detection was by a UV detector at 215 nanometers and elution with a mobil phase of 95% hexane and 5% tert-butylmethyl ether at a flow rate of 1.0 mL per minute. The samples were placed on the column diluted in 90% hexane, 5% isopropanol and 5% tert-butylmethyl ether.

EXAMPLE 8

Following the procedures of the previous Examples, the compounds set forth in Tables 1 through 13 can be prepared.

TABLE 1

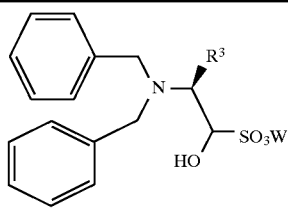

| Entry | R³ | W |
|---|---|---|
| 1 | isobutyl | Na |
| 2 | butyl | Na |

TABLE 1-continued

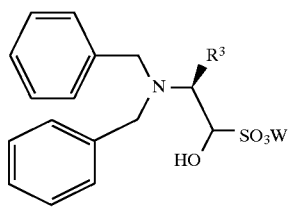

| Entry | R³ | W |
|---|---|---|
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 2

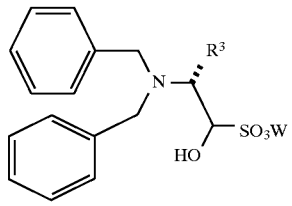

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 3

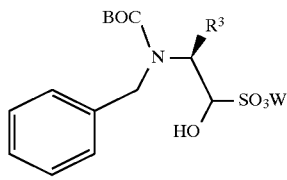

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 4

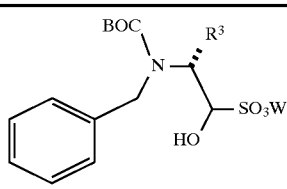

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 5

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 6

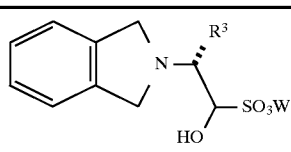

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 7

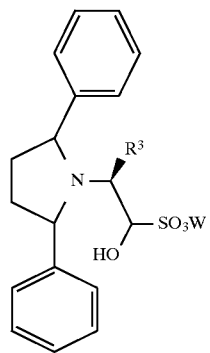

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxyethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 8

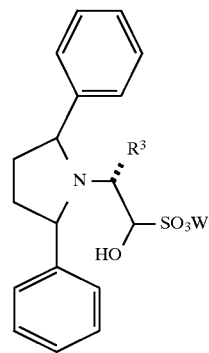

| Entry | R³ | W |
|---|---|---|
| 1 | isobutyl | Na |
| 2 | butyl | Na |
| 3 | sec-butyl | K |
| 4 | ethyl | Na |
| 5 | benzyl | Li |
| 6 | 4-hydroxyphenylmethyl | Na |
| 7 | hydroxymethyl | Na |
| 8 | 2-(methylthio)ethyl | K |
| 9 | 4-(BOC-amino)butyl | Na |
| 10 | aminocarbonylmethyl | Li |
| 11 | N-BOC-imidazol-2-ylmethyl | Na |
| 12 | 4-hydroxyphenyl | Na |
| 13 | hydrogen | Na |
| 14 | methyl | Na |
| 15 | 4-fluorophenylmethyl | K |
| 16 | cyanomethyl | K |
| 17 | bromomethyl | Na |
| 18 | trifluoromethyl | Li |
| 19 | phenoxymethyl | K |
| 20 | phenylthiomethyl | Na |
| 21 | phenyl | Li |
| 22 | 4-pyridyl | K |
| 23 | cyclohexyl | Na |
| 24 | cyclohexylmethyl | K |

TABLE 9

Entry

TABLE 9-continued

Entry

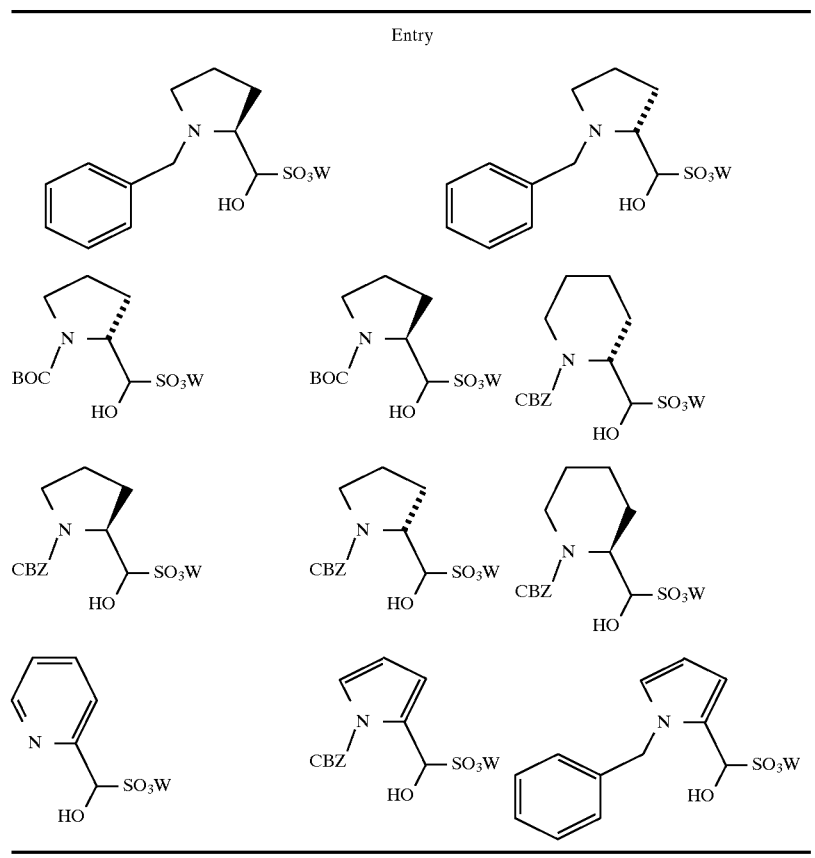

| TABLE 10 | | |
|---|---|---|

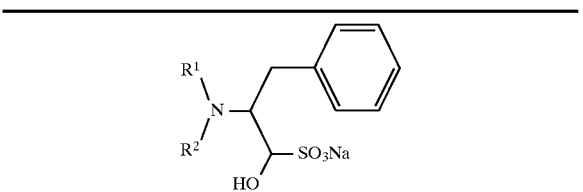

| Entry | R¹ | R² |
|---|---|---|
| 1 | methyl | benzyl |
| 2 | 2-cyclohexenylmethyl | 2-cyclohexenylmethyl |
| 3 | 2-propenyl | 2-propenyl |
| 4 | benzoyl | hydrogen |
| 5 | 2-pyridylmethoxycarbonyl | hydrogen |
| 6 | trifluoroacetyl | hydrogen |
| 7 | diphenylmethyl | 2-naphthylmethyl |
| 8 | isobutyl | isobutyl |
| 9 | ethyl | propenyl |
| 10 | 2-cyclohexenylmethyl | benzyl |
| 11 | acetyl | methyl |
| 12 | ethyl | ethyl |
| 13 | 2-pyridylmethoxycarbonyl | butyl |
| 14 | benzyl | cyclohexyl |
| 15 | 4-methoxybenzyloxycarbonyl | cyclopropyl |
| 16 | benzyloxycarbonyl | phenyl |
| 17 | 2-naphthylmethyl | 4-methoxyphenyl |
| 18 | 2-tetrahydrofuranoxycarbonyl | hydrogen |
| 19 | 2-thienylmethoxycarbonyl | methyl |
| 20 | R¹R²N = pyrrolyl | |
| 21 | R¹R²N = morpholinyl | |
| 22 | R¹R²N = piperidinyl | |

TABLE 10-continued

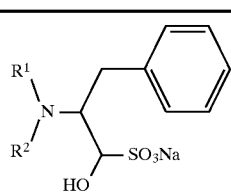

| Entry | R¹ | R² |
|---|---|---|
| 23 | R¹R²N = succinimido | |

TABLE 11

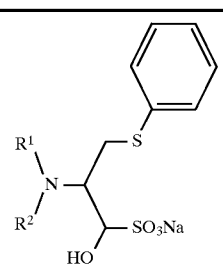

| Entry | R¹ | R² |
|---|---|---|
| 1 | methyl | benzyl |
| 2 | 2-cyclohexenylmethyl | 2-cyclohexenylmethyl |

TABLE 11-continued

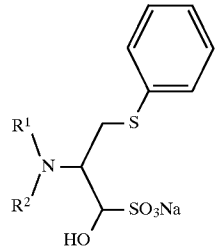

| Entry | R¹ | R² |
|---|---|---|
| 3 | 2-propenyl | 2-propenyl |
| 4 | benzoyl | hydrogen |
| 5 | 2-pyridylmethoxycarbonyl | hydrogen |
| 6 | trifluoroacetyl | hydrogen |
| 7 | diphenylmethyl | 2-naphthylmethyl |
| 8 | isobutyl | isobutyl |
| 9 | ethyl | propenyl |
| 10 | 2-cyclohexenylmethyl | benzyl |
| 11 | acetyl | methyl |
| 12 | ethyl | ethyl |
| 13 | 2-pyridylmethoxycarbonyl | butyl |
| 14 | benzyl | cyclohexyl |
| 15 | 4-methoxybenzyloxycarbonyl | cyclopropyl |
| 16 | benzyloxycarbonyl | phenyl |
| 17 | 2-naphthylmethyl | 4-methoxyphenyl |
| 18 | 2-tetrahydrofuranoxycarbonyl | hydrogen |
| 19 | 2-thienylmethoxycarbonyl | methyl |
| 20 | R¹R²N = pyrrolyl | |
| 21 | R¹R²N = morpholinyl | |
| 22 | R¹R²N = piperidinyl | |
| 23 | R¹R²N = succinimido | |

TABLE 12

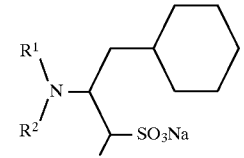

| Entry | R¹ | R² |
|---|---|---|
| 1 | methyl | benzyl |
| 2 | 2-cyclohexenylmethyl | 2-cyclohexenylmethyl |
| 3 | 2-propenyl | 2-propenyl |
| 4 | benzoyl | hydrogen |
| 5 | 2-pyridylmethoxycarbonyl | hydrogen |
| 6 | trifluoroacetyl | hydrogen |
| 7 | diphenylmethyl | 2-naphthylmethyl |
| 8 | isobutyl | isobutyl |
| 9 | ethyl | propenyl |
| 10 | 2-cyclohexenylmethyl | benzyl |
| 11 | acetyl | methyl |
| 12 | ethyl | ethyl |
| 13 | 2-pyridylmethoxycarbonyl | butyl |
| 14 | benzyl | cyclohexyl |
| 15 | 4-methoxybenzyloxycarbonyl | cyclopropyl |
| 16 | benzyloxycarbonyl | phenyl |
| 17 | 2-naphthylmethyl | 4-methoxyphenyl |
| 18 | 2-tetrahydrofuranoxycarbonyl | hydrogen |
| 19 | 2-thienylmethoxycarbonyl | methyl |
| 20 | R¹R²N = pyrrolyl | |
| 21 | R¹R²N = morpholinyl | |
| 22 | R¹R²N = piperidinyl | |
| 23 | R¹R²N = succinimido | |

TABLE 13

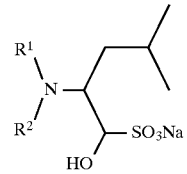

| Entry | R¹ | R² |
|---|---|---|
| 1 | methyl | benzyl |
| 2 | 2-cyclohexenylmethyl | 2-cyclohexenylmethyl |
| 3 | 2-propenyl | 2-propenyl |
| 4 | benzoyl | hydrogen |
| 5 | 2-pyridylmethoxycarbonyl | hydrogen |
| 6 | trifluoroacetyl | hydrogen |
| 7 | diphenylmethyl | 2-naphthylmethyl |
| 8 | isobutyl | isobutyl |
| 9 | ethyl | propenyl |
| 10 | 2-cyclohexenylmethyl | benzyl |
| 11 | acetyl | methyl |
| 12 | ethyl | ethyl |
| 13 | 2-pyridylmethoxycarbonyl | butyl |
| 14 | benzyl | cyclohexyl |
| 15 | 4-methoxybenzyloxycarbonyl | cyclopropyl |
| 16 | benzyloxycarbonyl | phenyl |
| 17 | 2-naphthylmethyl | 4-methoxyphenyl |
| 18 | 2-tetrahydrofuranoxycarbonyl | hydrogen |
| 19 | 2-thienylmethoxycarbonyl | methyl |
| 20 | R¹R²N = pyrrolyl | |
| 21 | R¹R²N = morpholinyl | |
| 22 | R¹R²N = piperidinyl | |
| 23 | R¹R²N = succinimido | |

EXAMPLE 9

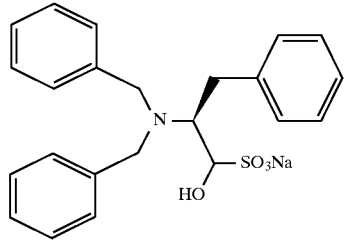

Determination of the stability of 2S-[bis(phenylmethyl)amino]-3-phenylpropanal and 2S-[bis(phenylmethyl)amino]-1-hydroxy-3-phenylpropylsulfonic acid, sodium salt 2S-[bis(phenylmethyl)amino]-1-hydroxy-3-phenylpropylsulfonic acid, sodium salt was stored at ambient temperature in a capped, brown glass bottle ("Salt Sample") and periodically samples of the salt was converted into 2S-[bis(phenylmethyl)amino]-3-phenylpropanal by the method of Example 7. The experiment extended through 61 days with purity determinations made on days 0 (t=0), 3 (t=3), 6 (t=6), 18 (t=18) and 61 (t=61). A sample of the salt was treated with aqueous potassium carbonate and extracted with ethyl acetate on day 0. The ethyl acetate was removed under reduced pressure to provide the aldehyde and this sample was used as a t=0 (day 1) reference standard for the stability determination ("Aldehyde Sample"). The t=0 sample of the aldehyde was then stored at ambient temperature in a capped, brown glass bottle side by side with the stored sample of the salt. The purity of the salt was then measured on days 3 (t=3), 8 (t=8), 15 (t=15) and 21 (t=21).

The identity and purity of all samples was determined by HPLC by the method of Example 7. The results of these studies are shown in Table 14.

TABLE 14

| Day (t =) | Aldehyde Sample (% aldehyde remaining) | Salt Sample (% aldehyde remaining) |
| --- | --- | --- |
| 0 | 99 | 99 |
| 3 | 94 | 99 |
| 6 | — | 100 |
| 8 | 64 | — |
| 15 | 23 | — |
| 18 | 10 | — |
| 21 | — | 99 |
| 61 | — | 99 |

The foregoing is merely illustrative of the invention and is not intended to limit the invention to the disclosed compounds. Variations and changes which are obvious to one skilled in the art are intended to be within the scope and nature of the invention which are defined in the appended claims. From the foregoing description, one skilled in the art can easily ascertain the essential characteristics of this invention, and without departing from the spirit and scope thereof, can make various changes and modifications of the invention to adapt it to various usages and conditions.

What is claimed is:

1. Compound represented by the formula:

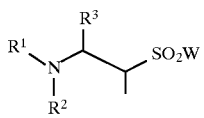

wherein W represents a cation which is capable of forming a sulfate salt;

$R^1$ represents alkyl, alkenyl, alkyl substituted with one or more aryl radicals, cycloalkenylalkyl, alkanoyl, haloalkanoyl, aroyl, alkoxycarbonyl, aralkoxycarbonyl, heteroaralkoxycarbonyl or 9-phenylfluoren-9-yl radicals;

$R^2$ represents hydrogen, alkyl, alkenyl, aralkyl, cycloalkyl, cycloalkenylalkyl or aryl radicals; or —$NR^1R^2$ represents heterocyclo or heteroaryl radicals; and $R^3$ represents alkyl, haloalkyl, cyanoalkyl, hydroxyalkyl, alkoxyalkyl, aryloxyalkyl, alkylthioalkyl, arylthioalkyl, aryl, aralkyl, heteroaryl, heteroaralkyl, cycloalkyl or cycloalkylalkyl radicals; or $R^2$ and $R^3$ together with nitrogen atom and the carbon atom to which they are bonded form a heterocyclo radical.

2. Compound of claim 1 wherein

W represents a metal cation or a quaternary amine cation which is capable of forming a sulfate salt;

$R^1$ represents alkyl of 1–8 carbon atoms, alkenyl of 2–8 carbon atoms, alkyl of 1–3 carbon atoms substituted with 1–3 aryl radicals, alkyl of 1–3 carbon atoms substituted with a cycloalkenyl radical of 3–8 ring members, alkanoyl of 1–4 alkyl carbon atoms, haloalkanoyl of 1–4 alkyl carbon atoms and 1–3 halo radicals, aroyl, alkoxycarbonyl of 1–8 alkyl carbon atoms, arylmethoxycarbonyl, heteroarylmethoxycarbonyl or 9-phenylfluoren-9-yl radicals;

$R^2$ represents hydrogen, alkyl of 1–8 carbon atoms, alkenyl of 2–8 carbon atoms, alkyl of 1–3 carbon atoms substituted with an aryl radical, cycloalkyl of 3–8 ring members, alkyl of 1–3 carbon atoms substituted with a cycloalkenyl radical of 3–8 ring members, or aryl radicals; or —$NR^1R^2$ represents 5–6 ring membered heterocyclo, 5–6 ring membered heteroaryl, benzo fused 5–6 ring membered heterocyclo or benzo fused 5–6 ring membered heteroaryl radicals; and $R^3$ represents alkyl radical of 1 to 5 carbon atoms, haloalkyl radical of 1 to 5 carbon atoms, cyanoalkyl radical of 1 to 5 alkyl carbon atoms, hydroxyalkyl radical of 1 to 5 alkyl carbon atoms, alkoxyalkyl radical of 1 to 5 alkyl carbon atoms and 1–3 alkoxy carbon atoms, aryloxyalkyl radical of 1 to 5 alkyl carbon atoms, alkylthioalkyl radical of 1 to 5 alkyl carbon atoms and 1–3 alkylthio carbon atoms, arylthioalkyl radical of 1 to 5 alkyl carbon atoms, aryl radical, aralkyl radical of 1 to 5 alkyl carbon atoms, heteroaralkyl radical of 1 to 5 alkyl carbon atoms and 5–6 ring members and benzo fused 5–6 ring members, cycloalkyl radical of 3–8 ring members, or cycloalkylalkyl radical of 1 to 5 alkyl carbon atoms and 3–8 ring members; or $R^2$ and $R^3$ together with nitrogen atom and the carbon atom to which they are bonded form a 5–6 ring membered heterocyclo radical or a benzo fused 5–6 ring membered heterocyclo radical.

3. Compound of claim 2 wherein

W represents a cation of lithium, sodium, potassium, calcium, manganese, magnesium, barium, chromium, iron, nickel, cobalt, copper, zinc, cadmium, tin or silver;

$R^1$ represents alkyl of 1–5 carbon atoms, alkenyl of 2–5 carbon atoms, alkyl of 1–2 carbon atoms substituted with 1–3 aryl radicals, alkyl of 1–2 carbon atoms substituted with a cycloalkenyl radical of 5–6 ring members, alkanoyl of 1–4 alkyl carbon atoms, haloalkanoyl of 1–2 alkyl carbon atoms and 1–3 halo radicals, aroyl, alkoxycarbonyl of 1–5 alkyl carbon atoms, arylmethoxycarbonyl, heteroarylmethoxycarbonyl or 9-phenylfluoren-9-yl radicals;

$R^2$ represents hydrogen, alkyl of 1–5 carbon atoms, alkenyl of 2–5 carbon atoms, alkyl of 1–2 carbon atoms substituted with an aryl radical, cycloalkyl of 3–6 ring members, alkyl of 1–2 carbon atoms substituted with a cycloalkenyl radical of 5–6 ring members, or aryl radicals; or —$NR^1R^2$ represents 5–6 ring membered heterocyclo or benzo fused 5–6 ring membered heterocyclo radicals; and $R^3$ represents alkyl radical of 1 to 5 carbon atoms, hydroxyalkyl radical of 1 to 3 alkyl carbon atoms, methoxyalkyl radical of 1 to 3 alkyl carbon atoms, phenoxyalkyl radical of 1 to 3 alkyl carbon atoms, methylthioalkyl radical of 1 to 3 alkyl carbon atoms, arylthioalkyl radical of 1 to 3 alkyl carbon atoms, aryl radical, aralkyl radical of 1 to 3 alkyl carbon atoms, heteroaralkyl radical of 1 to 3 alkyl carbon atoms and 5–6 ring members and benzo fused 5–6 ring members, cycloalkyl radical of 5–6 ring members, or cycloalkylalkyl radical of 1 to 3 alkyl carbon atoms and 3–6 ring members; or $R^2$ and $R^3$ together with nitrogen atom and the carbon atom to which they are bonded form a 5–6 ring membered heterocyclo radical optionally substituted with hydroxy radical.

4. Compound of claim 3 wherein

W represents a cation of lithium, sodium, potassium, calcium, magnesium, barium, iron, nickel, copper or zinc;

R¹ represents methyl, ethyl, ethenyl, propenyl, benzyl, diphenylmethyl, naphthylmethyl, trityl, cyclohexenylmethyl, acetyl, butyryl, chloroacetyl, fluoroacetyl, difluoroacetyl, trifluoroacetyl, benzoyl, 2-methylbenzoyl, 2,6-dimethylbenzoyl, 2,4,6-trimethylbenzoyl, 2,4,6-triisopropylbenzoyl, methoxycarbonyl, ethoxycarbonyl, tert-butoxycarbonyl, phenylmethoxycarbonyl, (2-methylphenyl)methoxycarbonyl, (4-methylphenyl)methoxycarbonyl, (4-methoxyphenyl)methoxycarbonyl, pyridylmethoxycarbonyl, or 9-phenylfluoren-9-yl radicals;

R² represents hydrogen, methyl, ethyl, ethenyl, propenyl, cyclohexenylmethyl, benzyl or naphthylmethyl radicals; or —NR¹R² represents pyrrolidinyl, piperidinyl, pyrrolyl, 2-isoindolinyl, phthalimidyl, succinimidyl or maleimidyl radicals; and R³ represents methyl, ethyl, propyl, isopropyl, butyl, isobutyl, sec-butyl, tert-butyl, hydroxymethyl, hydroxyethyl, methoxyethyl, phenoxymethyl, methylthioethyl, phenylthiomethyl, phenylthioethyl, naphthylthiomethyl, naphthylthioethyl, phenyl, naphthyl, benzyl, 4-fluorobenzyl, 4-methylbenzyl, 4-methoxybenzyl, naphthylmethyl, imidazolylmethyl, indolylmethyl, cyclohexyl or cyclohexylmethyl radicals; or R² and R³ together with nitrogen atom and the carbon atom to which they are bonded form pyrrolidinyl, 3-hydroxypyrrolidinyl, 4-hydroxypyrrolidinyl, piperidinyl, 3-hydroxypiperidinyl, 4-hydroxypiperidinyl or 5-hydroxypiperidinyl radicals.

5. Compound of claim 4 wherein
W represents a cation of lithium, sodium or potassium;
R¹ represents methyl, ethyl, benzyl, diphenylmethyl, naphthylmethyl, trityl, trifluoroacetyl, tert-butoxycarbonyl, phenylmethoxycarbonyl or (4-methoxyphenyl)methoxycarbonyl radicals;
R² represents hydrogen, methyl, ethyl or benzyl radicals; or —NR¹R² represents 2-isoindolinyl, phthalimidyl, succinimidyl or maleimidyl radicals; and
R³ represents methyl, isopropyl, butyl, isobutyl, sec-butyl, tert-butyl, methylthioethyl, phenylthiomethyl, naphthylthiomethyl, benzyl, 4-fluorobenzyl, 4-methylbenzyl, 4-methoxybenzyl, naphthylmethyl, imidazolylmethyl or cyclohexylmethyl radicals; or
R² and R³ together with nitrogen atom and the carbon atom to which they are bonded form pyrrolidinyl or piperidinyl radicals.

6. Compound of claim 1 which is 2S-[bis(phenylmethyl)amino]-1-hydroxy-3-phenylpropylsulfonic acid, sodium salt.

7. Process of preparing a compound formula

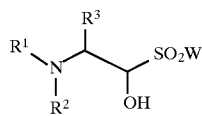

wherein W represents a cation which is capable of forming a sulfate salt;
R¹ represents alkyl, alkenyl, alkyl substituted with one or more aryl radicals, cycloalkenylalkyl, alkanoyl, haloalkanoyl, aroyl, alkoxycarbonyl, aralkoxycarbonyl, heteroaralkoxycarbonyl or 9-phenylfluoren-9-yl radicals;

R² represents hydrogen, alkyl, alkenyl, aralkyl, cycloalkyl, cycloalkenylalkyl or aryl radicals; or —NR¹R² represents heterocyclo or heteroaryl radicals; and R³ represents alkyl, haloalkyl, cyanoalkyl, hydroxyalkyl, alkoxyalkyl, aryloxyalkyl, alkylthioalkyl, arylthioalkyl, aryl, aralkyl, heteroaryl, heteroaralkyl, cycloalkyl or cycloalkylalkyl radicals; or R² and R³ together with nitrogen atom and the carbon atom to which they are bonded form a heterocyclo radical;

wherein said process comprises treating an aldehyde represented by the formula

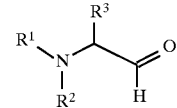

wherein R¹, R² and R³ are as defined above, in an organic solvent with an aqueous solution of HSO₃W, wherein W is as defined above.

8. Process of claim 7 wherein W represents a metal cation or a quaternary amine cation which is capable of forming a sulfate salt;
R¹ represents alkyl of 1–8 carbon atoms, alkenyl of 2–8 carbon atoms, alkyl of 1–3 carbon atoms substituted with 1–3 aryl radicals, alkyl of 1–3 carbon atoms substituted with a cycloalkenyl radical of 3–8 ring members, alkanoyl of 1–4 alkyl carbon atoms, haloalkanoyl of 1–4 alkyl carbon atoms and 1–3 halo radicals, aroyl, alkoxycarbonyl of 1–8 alkyl carbon atoms, arylmethoxycarbonyl, heteroarylmethoxycarbonyl or 9-phenylfluoren-9-yl radicals;
R² represents hydrogen, alkyl of 1–8 carbon atoms, alkenyl of 2–8 carbon atoms, alkyl of 1–3 carbon atoms substituted with an aryl radical, cycloalkyl of 3–8 ring members, alkyl of 1–3 carbon atoms substituted with a cycloalkenyl radical of 3–8 ring members, or aryl radicals; or —NR¹R² represents 5–6 ring membered heterocyclo, 5–6 ring membered heteroaryl, benzo fused 5–6 ring membered heterocyclo or benzo fused 5–6 ring membered heteroaryl radicals; and
R³ represents alkyl radical of 1 to 5 carbon atoms, haloalkyl radical of 1 to 5 carbon atoms, cyanoalkyl radical of 1 to 5 alkyl carbon atoms, hydroxyalkyl radical of 1 to 5 alkyl carbon atoms, alkoxyalkyl radical of 1 to 5 alkyl carbon atoms and 1–3 alkoxy carbon atoms, aryloxyalkyl radical of 1 to 5 alkyl carbon atoms, alkylthioalkyl radical of 1 to 5 alkyl carbon atoms and 1–3 alkylthio carbon atoms, arylthioalkyl radical of 1 to 5 alkyl carbon atoms, aryl radical, aralkyl radical of 1 to 5 alkyl carbon atoms, heteroaralkyl radical of 1 to 5 alkyl carbon atoms and 5–6 ring members and benzo fused 5–6 ring members, cycloalkyl radical of 3–8 ring members, or cycloalkylalkyl radical of 1 to 5 alkyl carbon atoms and 3–8 ring members; or
R² and R³ together with nitrogen atom and the carbon atom to which they are bonded form a 5–6 ring membered heterocyclo radical or a benzo fused 5–6 ring membered heterocyclo radical.

9. Process of claim 8 wherein W represents a cation of lithium, sodium, potassium, calcium, manganese, magnesium, barium, chromium, iron, nickel, cobalt, copper, zinc, cadmium, tin or silver;

R$^1$ represents alkyl of 1–5 carbon atoms, alkenyl of 2–5 carbon atoms, alkyl of 1–2 carbon atoms substituted with 1–3 aryl radicals, alkyl of 1–2 carbon atoms substituted with a cycloalkenyl radical of 5–6 ring members, alkanoyl of 1–4 alkyl carbon atoms, haloalkanoyl of 1–2 alkyl carbon atoms and 1–3 halo radicals, 4aroyl, alkoxycarbonyl of 1–5 alkyl carbon atoms, arylmethoxycarbonyl, heteroarylmethoxycarbonyl or 9-phenylfluoren-9-yl radicals;

R$^2$ represents hydrogen, alkyl of 1–5 carbon atoms, alkenyl of 2–5 carbon atoms, alkyl of 1–2 carbon atoms substituted with an aryl radical, cycloalkyl of 3–6 ring members, alkyl of 1–2 carbon atoms substituted with a cycloalkenyl radical of 5–6 ring members, or aryl radicals; or —NR$^1$R$^2$ represents 5–6 ring membered heterocyclo or benzo fused 5–6 ring membered heterocyclo radicals; and R$^3$ represent s alkyl radical of 1 to 5 carbon atoms, hydroxyalkyl radical of 1 to 3 alkyl carbon atoms, methoxyalkyl radical of 1 to 3 alkyl carbon atoms, phenoxyalkyl radical of 1 to 3 alkyl carbon atoms, methylthioalkyl radical of 1 to 3 alkyl carbon atoms, arylthioalkyl radical of 1 to 3 alkyl carbon atoms, aryl radical, aralkyl radical of 1 to 3 alkyl carbon atoms, heteroaralkyl radical of 1 to 3 alkyl carbon atoms and 5–6 ring members and benzo fused 5–6 ring members, cycloalkyl radical of 5–6 ring members, or cycloalkylalkyl radical of 1 to 3 alkyl carbon atoms and 3–6 ring members; or R$^2$ and R$^3$ together with nitrogen atom and the carbon atom to which they are bonded form a 5–6 ring membered heterocyclo radical optionally substituted with hydroxy radical.

10. Process of claim 9 wherein W represents a cation of lithium, sodium, potassium, calcium, magnesium, barium, iron, nickel, copper or zinc;

R$^1$ represents methyl, ethyl, ethenyl, propenyl, benzyl, diphenylmethyl, naphthylmethyl, trityl, cyclohexenylmethyl, acetyl, butyryl, chloroacetyl, fluoroacetyl, difluoroacetyl, trifluoroacetyl, benzoyl, 2-methylbenzoyl, 2,6-dimethylbenzoyl, 2,4,6-trimethylbenzoyl, 2,4,6-triisopropylbenzoyl, methoxycarbonyl, ethoxycarbonyl, tert-butoxycarbonyl, phenylmethoxycarbonyl, (2-methylphenyl)methoxycarbonyl, (4-methylphenyl)methoxycarbonyl, (4-methoxyphenyl)methoxycarbonyl, pyridylmethoxycarbonyl, or 9-phenylfluoren-9-yl radicals;

R$^2$ represents hydrogen, methyl, ethyl, ethenyl, propenyl, cyclohexenylmethyl, benzyl or naphthylmethyl radicals; or —NR$^1$R$^2$ represents pyrrolidinyl, piperidinyl, pyrrolyl, 2-isoindolinyl, phthalimidyl, succinimidyl or maleimidyl radicals; and R$^3$ represents methyl, ethyl, propyl, isopropyl, butyl, isobutyl, sec-butyl, tert-butyl, hydroxymethyl, hydroxyethyl, methoxyethyl, phenoxymethyl, methylthioethyl, phenylthiomethyl, phenylthioethyl, naphthylthiomethyl, naphthylthioethyl, phenyl, naphthyl, benzyl, 4-fluorobenzyl, 4-methylbenzyl, 4-methoxybenzyl, naphthylmethyl, imidazolylmethyl, indolylmethyl, cyclohexyl or cyclohexylmethyl radicals; or R$^2$ and R$^3$ together with nitrogen atom and the carbon atom to which they are bonded form pyrrolidinyl, 3-hydroxypyrrolidinyl, 4-hydroxypyrrolidinyl, piperidinyl, 3-hydroxypiperidinyl, 4-hydroxypiperidinyl or 5-hydroxypiperidinyl radicals.

11. Process of claim 10 wherein W represents a cation of lithium, sodium or potassium;

R$^1$ represents methyl, ethyl, benzyl, diphenylmethyl, naphthylmethyl, trityl, trifluoroacetyl, tert-butoxycarbonyl, phenylmethoxycarbonyl or (4-methoxyphenyl)methoxycarbonyl radicals;

R$^2$ represents hydrogen, methyl, ethyl or benzyl radicals; or —NR$^1$R$^2$ represents 2-isoindolinyl, phthalimidyl, succinimidyl or maleimidyl radicals; and R$^3$ represents methyl, isopropyl, butyl, isobutyl, sec-butyl, tert-butyl, methylthioethyl, phenylthiomethyl, naphthylthiomethyl, benzyl, 4-fluorobenzyl, 4-methylbenzyl, 4-methoxybenzyl, naphthylmethyl, imidazolylmethyl or cyclohexylmethyl radicals; or R$^2$ and R$^3$ together with nitrogen atom and the carbon atom to which they are bonded form pyrrolidinyl or piperidinyl radicals.

12. Process of claim 11 wherein 2S-[bis(phenylmethyl)amino]-1-hydroxy-3-phenylpropylsulfonic acid, sodium salt is prepared from 2S-[bis(phenylmethyl)amino]-3-phenylpropanal.

13. Process of claim 7 wherein said organic solvent is ethyl acetate, tetrahydrofuran, isopropyl acetate, methyl isobutyl ketone, methyl, ethyl ketone, acetone, dimethoxyethane, dimethoxymethane, dioxane or methyl tert-butylether.

14. Process of claim 7 wherein the equivalence ratio of bisulfite salt HSO$_3$W to aldehyde is within the range of about 1:1 to about 1:10.

15. Process of claim 7 wherein the equivalence ratio of bisulfite salt HSO$_3$W to aldehyde is the range of about 1:1 to about 1:5.

16. Process of claim 7 wherein the equivalence ratio of bisulfite salt HSO$_3$W to aldehyde is the range of about 1:1 to about 1:2.

* * * * *

UNITED STATES PATENT AND TRADEMARK OFFICE
CERTIFICATE OF CORRECTION

PATENT NO. : 5,847,201
DATED : December 8, 1998
INVENTOR(S) : Joseph J. Wieczorek Page 1 of 1

It is certified that error appears in the above-identified patent and that said Letters Patent is hereby corrected as shown below:

Column 31, claim 1,
Line 30, the recited formula

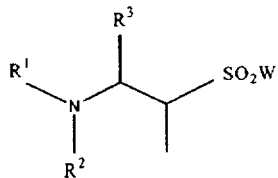

Column 33, claim 7,
Line 55, the recited formula

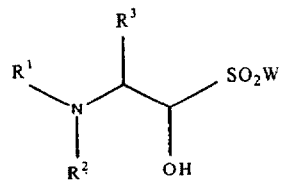

have both been replaced with

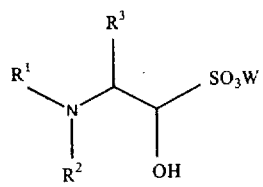

Signed and Sealed this

Twenty-sixth Day of March, 2002

Attest:

*Attesting Officer*

JAMES E. ROGAN
*Director of the United States Patent and Trademark Office*